United States Patent
Yi et al.

(10) Patent No.: US 9,902,709 B2
(45) Date of Patent: Feb. 27, 2018

(54) POLYSUBSTITUTED PYRIDINE COMPOUND, PREPARATION METHOD, USE AND PHARMACEUTICAL COMPOSITION

(71) Applicants: PEKING UNIVERSITY FOUNDER GROUP CO., LTD., Beijing (CN); PKUCARE PHARMACEUTICAL R&D CENTER, Beijing (CN); PKU HEALTHCARE INDUSTRY GROUP CO., LTD., Beijing (CN)

(72) Inventors: Chongqin Yi, Beijing (CN); Heng Xu, Beijing (CN); Jing Tao, Beijing (CN); Songwen Lin, Beijing (CN); Fangbin Han, Beijing (CN)

(73) Assignees: PEKING UNIVERSITY FOUNDER GROUP CO., LTD., Beijing (CN); PKUCARE PHARMACEUTICAL R & D CENTER, Beijing (CN); PKU HEALTHCARE INDUSTRY GROUP CO., LTD., Beijing (CN)

( * ) Notice: Subject to any disclaimer, the term of this patent is extended or adjusted under 35 U.S.C. 154(b) by 0 days.

(21) Appl. No.: 15/302,723

(22) PCT Filed: Dec. 30, 2014

(86) PCT No.: PCT/CN2014/095461
§ 371 (c)(1),
(2) Date: Oct. 7, 2016

(87) PCT Pub. No.: WO2015/154535
PCT Pub. Date: Oct. 15, 2015

(65) Prior Publication Data
US 2017/0029404 A1    Feb. 2, 2017

(30) Foreign Application Priority Data

Apr. 8, 2014  (CN) .......................... 2014 1 0139359

(51) Int. Cl.
*A61K 31/4439*    (2006.01)
*C07D 401/04*    (2006.01)

(52) U.S. Cl.
CPC ........ *C07D 401/04* (2013.01); *A61K 31/4439* (2013.01)

(58) Field of Classification Search
USPC ........................................ 514/359, 385, 403
See application file for complete search history.

(56) References Cited

U.S. PATENT DOCUMENTS

| | | | |
|---|---|---|---|
| 2007/0155764 A1 | 7/2007 | Lang et al. | |
| 2008/0261961 A1* | 10/2008 | Flynn .................. | C07D 401/14 514/227.8 |
| 2011/0053905 A1 | 3/2011 | Guo et al. | |
| 2017/0066738 A1 | 3/2017 | Guo et al. | |

FOREIGN PATENT DOCUMENTS

| | | | |
|---|---|---|---|
| CN | 1341098 | 3/2002 | |
| CN | 1656073 | 8/2005 | |
| CN | 101801383 | 8/2010 | |
| CN | 102234270 | 11/2011 | |
| CN | 102532113 | 7/2012 | |
| CN | 102532113 A * | 7/2012 | ............ A61K 31/36 |
| CN | 102558144 | 7/2012 | |
| CN | 102686577 | 9/2012 | |
| JP | 2013-503901 A5 | 10/2013 | |
| KR | 10-2012-047313 A | 5/2012 | |
| WO | WO 2011-028995 A1 | 3/2011 | |
| WO | WO 2012/019015 | 2/2012 | |

OTHER PUBLICATIONS

Extended European Search Report for EP 14888830.8-1454/3130588 PCT/CN2014/095461, dated Aug. 7, 2017.
Wenhu Zhan et al., "Design, synthesis and antitumor activities of novel bis-aryl ureas derivatives of Raf kinase inhibitors," Bioorganic & Medicinal Chemistry vol. 20, No. 14, (May 22, 2012); pp. 4323-4329.
Japanese Office Action for JP2017-504218, dated Sep. 11, 2017.
Korean Office Action for KR 10-2016-7030986, dated Sep. 26, 2017.

* cited by examiner

*Primary Examiner* — Pancham Bakshi
(74) *Attorney, Agent, or Firm* — Brinks Gilson & Lione

(57) ABSTRACT

The present invention provides a polysubstituted pyridine compound of Formula I, a preparation method, a use and a pharmaceutical composition thereof. The polysubstituted pyridine compound of Formula I according to the present invention has an excellent anti-tumor effect, can inhibit various cell kinases simultaneously, has significantly excellent pharmacokinetic characteristics, and is very suitable for oral and intravenous administration. The pharmaceutical composition according to the present invention can be useful for treating tumors and cancers.

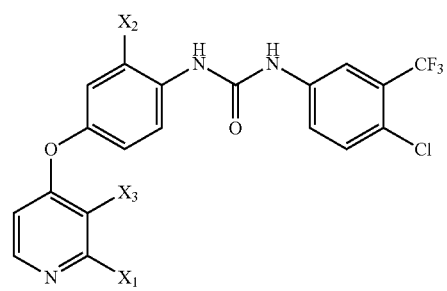

Formula I

4 Claims, 1 Drawing Sheet

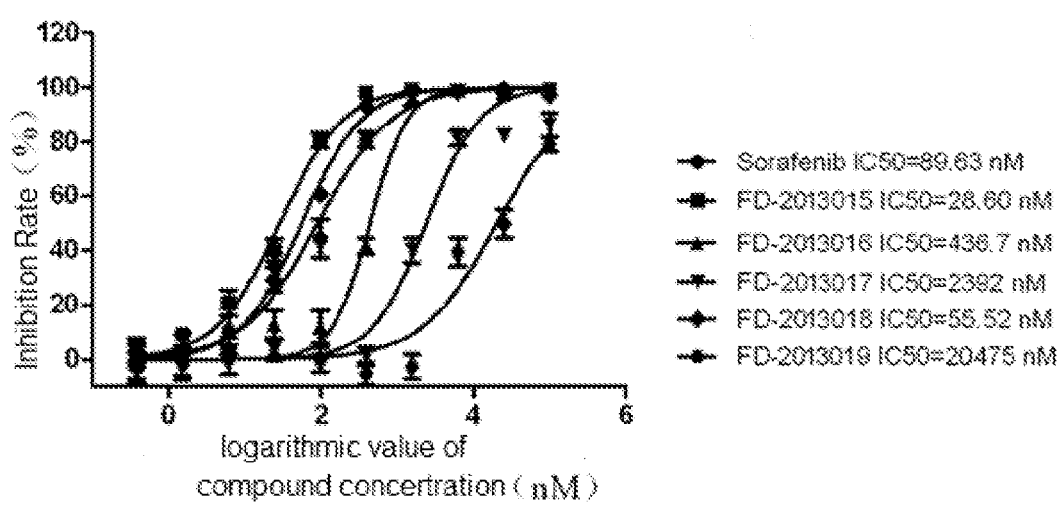

POLYSUBSTITUTED PYRIDINE COMPOUND, PREPARATION METHOD, USE AND PHARMACEUTICAL COMPOSITION

CROSS-REFERENCE TO RELATED APPLICATIONS

This application is a national application of PCT/CN2014/095461, filed on Dec. 30, 2014, which application claims a right of priority to Chinese Patent Application No. 201410139359.7, filed Apr. 8, 2014, both of which are incorporated herein by reference in their entirety.

TECHNICAL FIELD

The invention belongs to the field of pharmaceutical chemistry, particularly relates to a polysubstituted pyridine compound, a preparation method, a use and a pharmaceutical composition thereof.

BACKGROUND ART

It is very challenging and significant to research and develop antitumor drugs in the field of life science. In recent years, with the rapid development in molecular biology and deeper understanding on occurrence, development and mechanism of cancer, various basic processes, such as signal transduction in a malignant tumor cell, modulation of cell cycle, induction of apoptosis, angiogenesis and interaction between cell and extracellular matrix, are gradually elucidated. Therefore, it is one of the important areas in pharmaceutical research and development to look for novel antitumor drugs with high efficiency, low toxicity, and strong specificity, which selectively act on specific targets. Therefore, it leads to a new antitumor drug field—molecular targeted drugs.

Molecular targeted drugs refer to a class of drugs that are directed to receptors involved in cell cancerization or to key enzymes in transduction, and inhibit tumor growth in molecular level. They target the characteristic molecules of tumor cells, and play an antitumor role whilst reducing the toxic and side-effect on normal cells.

The balance between positive and negative regulators controls the angiogenesis of tumor, which promotes the growth and metastasis of tumor, thereby the development of angiogenesis inhibitors becomes one of hotspots in tumor research. VEGFR refers to a class of important tyrosine kinases. Many studies show that dysfunction in signal transduction pathway of VEGFR plays an important role in occurrence, growth and metastasis of tumor. VEGFR mainly include VEGFR21(Flt21), VEGFR22(KDR/Flt21) and VEGFR23(Flt24), which belong to tyrosine kinase receptors. VEGF exerts biological function by binding to two trans-membrane receptors of endothelial cell.

Signal transduction factors in cell differentiation include a lot of protein kinase families. During cell signal transduction, protein tyrosine kinases are very important as they can catalyze the transfer of a phosphate group from ATP to tyrosine residue of many important proteins to make them phosphorylated, which activates transduction by-pass, and affects cell growth, proliferation and differentiation. In many tumor cells, tyrosine kinase activity is abnormally increased. More than 50% oncogenes and products thereof have protein tyrosine kinase activity, and abnormal expression thereof would lead to the occurrence of tumor. In addition, the abnormal expression of the enzyme is also associated with tumor metastasis, tumor angiogenesis, and resistance of tumor to chemical therapy. Research on selective protein kinase inhibitors that can block or modify abnormal signal transduction is deemed to be a promising direction for development of drugs. Now, some protein kinase inhibitors and small-molecule therapeutic agents against different ATP-binding sites of protein kinases have been discovered and entered a clinic research phase, such as tyrosine kinase inhibitors.

Sorafenib (Trade name: Nexavar) developed by Bayer Pharmaceuticals is a multi-targeted drug approved as the first-line drug for treatment of advanced renal carcinoma by United States Food and Drug Administration (FDA) in December, 2005, and is the first multi-targeted drug approved for targeted therapy in clinic in the world. The Chinese patent application document CN1341098A discloses the chemical structure of Sorafenib, and the structure of Sorafenib is as follows:

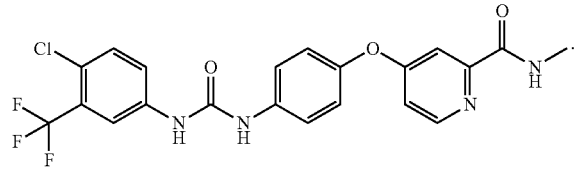 [SMILES: CNC(=O)c1cc(Oc2ccc(NC(=O)Nc3ccc(Cl)c(C(F)(F)F)c3)cc2)ccn1]

Before the invention, the inventor also submitted another Chinese patent application, and the patent application document CN102532113A (Application No.: 201110435847.9) discloses a compound of the following formula:

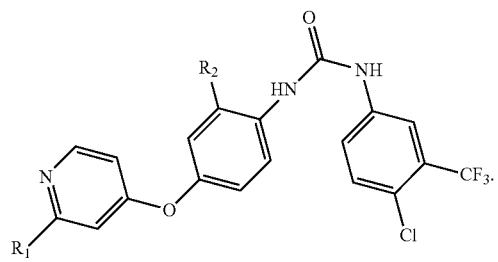

Since the existing antitumor drugs still fail to meet the needs of treating tumor diseases in human and other mammals, and the therapeutic effects of the commercially available antitumor drugs in clinic still fail to reach the desired level, there is still demand for more effective antitumor drugs.

CONTENTS OF INVENTION

In order to solve the foregoing problems in the prior art, the present invention provides a polysubstituted pyridine compound, a preparation method, a use and a pharmaceutical composition thereof.

In particular,

In a first aspect, the present invention provides a polysubstituted pyridine compound of Formula I, or a hydrate, a solvate or a pharmaceutically acceptable salt thereof:

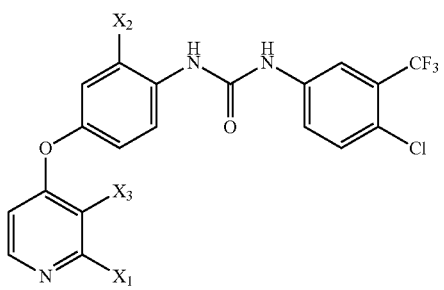

Formula I wherein:
X₁ is selected from a substituted or unsubstituted 5-membered heteroaromatic ring of Formula a;

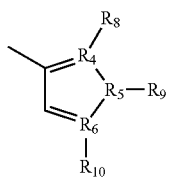

Formula a $R_4$, $R_5$ and $R_6$ each are independently selected from a group consisting of carbon atom, nitrogen atom, oxygen atom and sulfur atom, $R_8$, $R_9$ and $R_{10}$ each are independently selected from a group consisting of hydrogen, halogen, $C_1$-$C_4$alkyl and $C_1$-$C_4$alkoxyl;

$X_2$ is selected from a group consisting of F and H;

$X_3$ is selected from a group consisting of halogen, —CN, $C_1$-$C_4$alkyl, halogenated $C_1$-$C_4$alkyl, $C_1$-$C_4$alkoxyl, halogenated $C_1$-$C_4$alkoxyl and —$NR_{11}R_{12}$, wherein said $R_{11}$ and $R_{12}$ each are independently selected from a group consisting of hydrogen and $C_1$-$C_4$alkyl.

Preferably, $R_4$, $R_5$ and $R_6$ each are independently selected from a group consisting of carbon atom and nitrogen atom.

Preferably, $R_4$, $R_5$ and $R_6$ are not carbon atoms simultaneously.

Preferably, $R_4$, $R_5$ and $R_6$ are not nitrogen atoms simultaneously.

Preferably, $R_8$, $R_9$ and $R_{10}$ each are independently selected from a group consisting of hydrogen and methyl.

Preferably, $X_1$ is

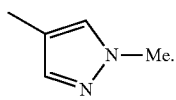

Preferably, $X_3$ is selected from a group consisting of F, Cl, Br, —$CF_3$, —CN, $C_1$-$C_2$alkyl, $C_1$-$C_2$alkoxyl and —$NR_{11}R_{12}$, wherein said $R_{11}$ and $R_{12}$ each are independently selected from a group consisting of hydrogen and $C_1$-$C_2$ alkyl.

Preferably, $X_3$ is selected from a group consisting of F, Cl and —CN.

Preferably, the polysubstituted pyridine compound of Formula I is selected from a group consisting of the following compounds:

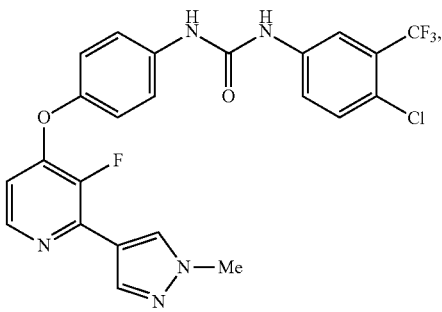

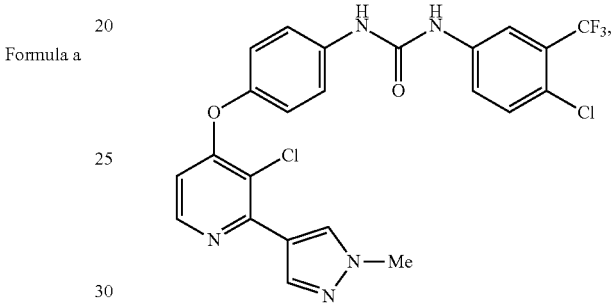

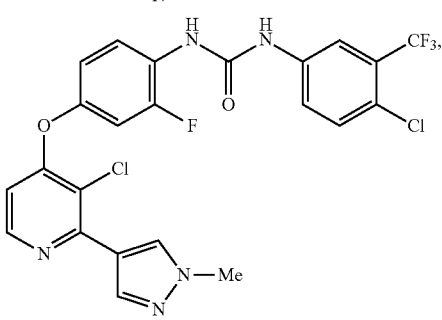

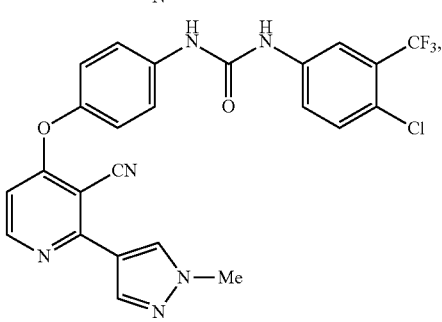

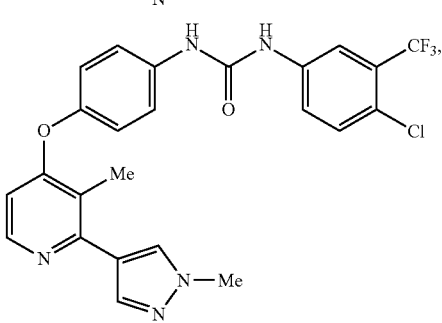

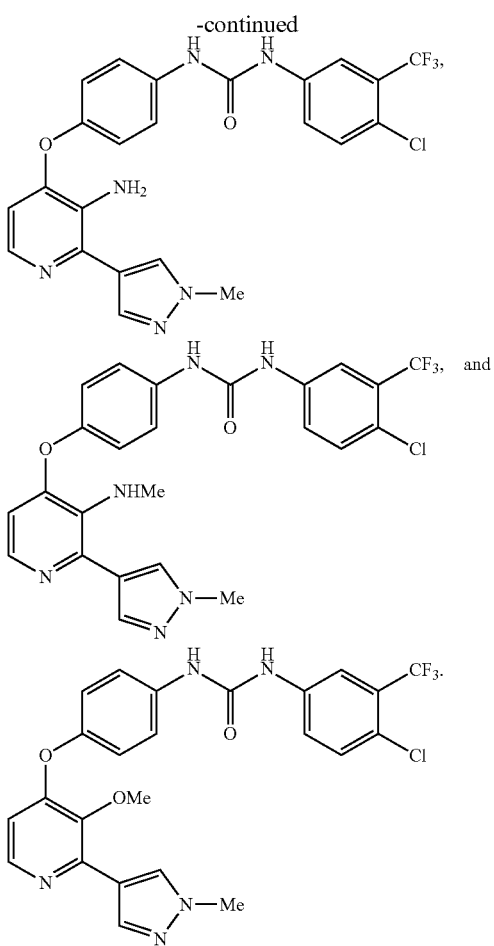

More preferably, the polysubstituted pyridine compound of Formula I is selected from a group consisting of the following compounds:

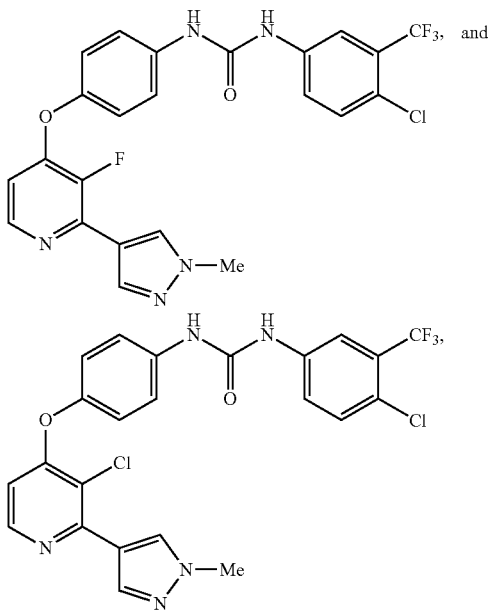

Preferably, the pharmaceutically acceptable salt of the polysubstituted pyridine compound of Formula I is selected from a group consisting of: hydrochloride, hydrobromide, sulphate, phosphate, methanesulfonate, trifluoromethanesulfonate, benzene sulfonate, p-toluenesulfonate, 1-naphthalenesulfonate, 2-naphthalenesulfonate, acetate, trifluoroacetate, malate, tartrate, citrate, lactate, oxalate, succinate, fumarate, maleate, benzoate, salicylate, phenyl acetate and mandelate.

The present invention further relates to a method for preparing said polysubstituted pyridine compound according to the present invention, comprising:

1) as shown in the following scheme, reacting a compound of Formula B with a compound of Formula C in the presence of potassium terb-butoxide as a base, to get a compound of Formula D:

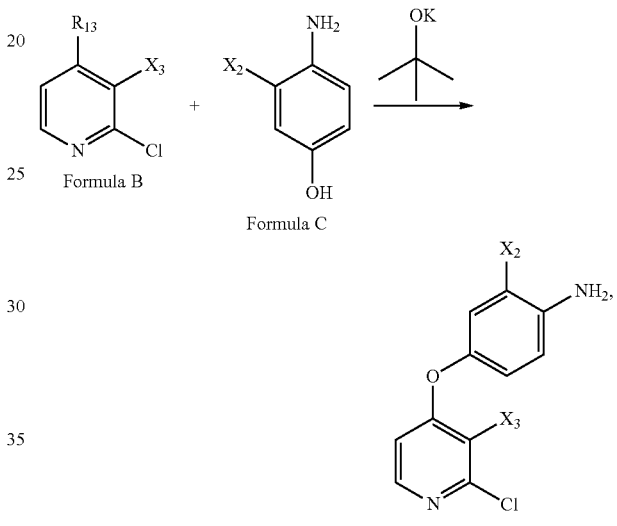

wherein $R_{13}$ is F, Cl, Br or I;

2) as shown in the following scheme, reacting the compound of Formula D with a compound of Formula E in the presence of tetrakis (triphenylphosphine) palladium or bis (triphenylphosphine)palladium(II) dichloride as a catalyst, to get a compound of Formula F:

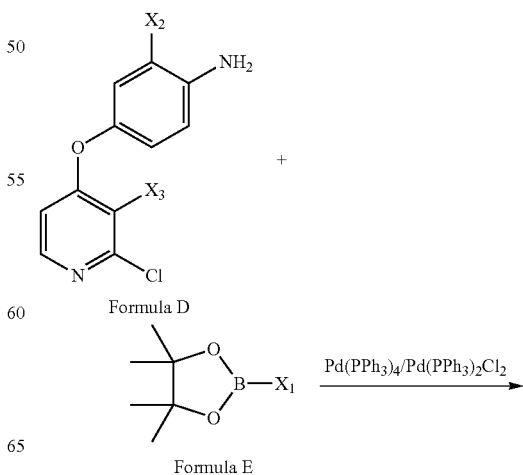

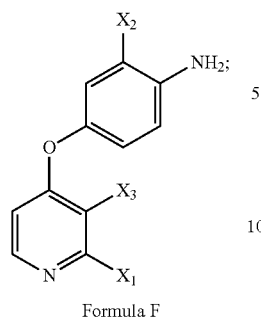

Formula F and 3) as shown in the following scheme, reacting the compound of Formula F with a compound of Formula G, to get the polysubstituted pyridine compound of Formula I:

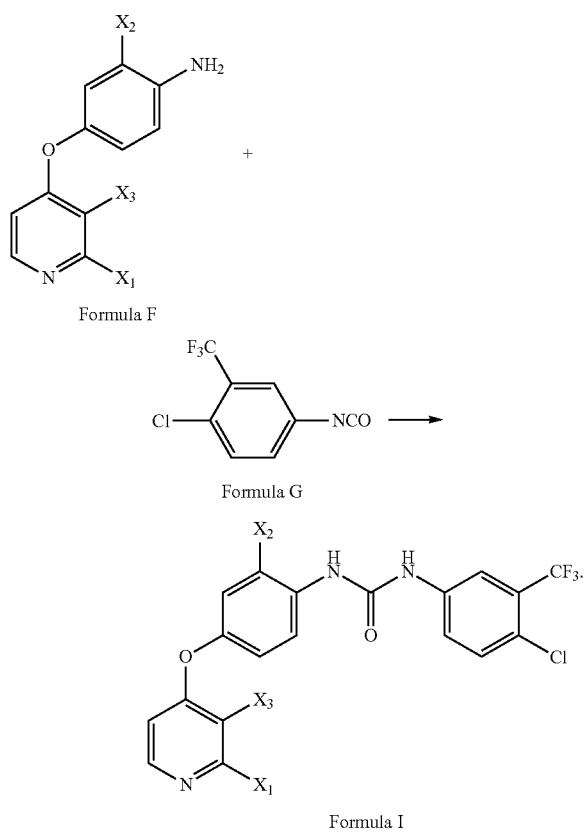

Preferably, said compound of Formula B is prepared by the following method:

a compound of Formula A is halogenated to get the compound of Formula B:

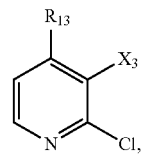

Formula A

Formula B

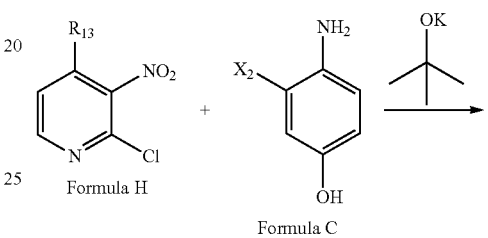

wherein $R_{13}$ is F, Cl, Br or I.

Preferably, when $X_3$ is $NH_2$, said preparation method comprises:

1) as shown in the following scheme, reacting a compound of Formula H with a compound of Formula C in the presence of potassium terb-butoxide as a catalyst, to get a compound of Formula W;

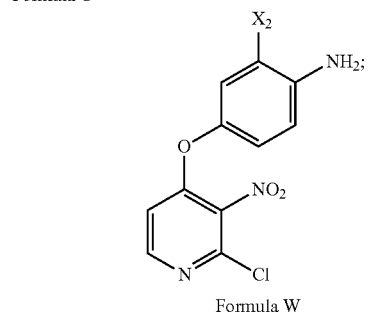

wherein $R_{13}$ is F, Cl, Br or I;

2) as shown in the following scheme, reacting the compound of Formula W with a compound of Formula E in the presence of the tetrakis(triphenylphosphine)palladium or bis(triphenylphosphine) palladium(II) dichloride as a catalyst, to get a compound of Formula J:

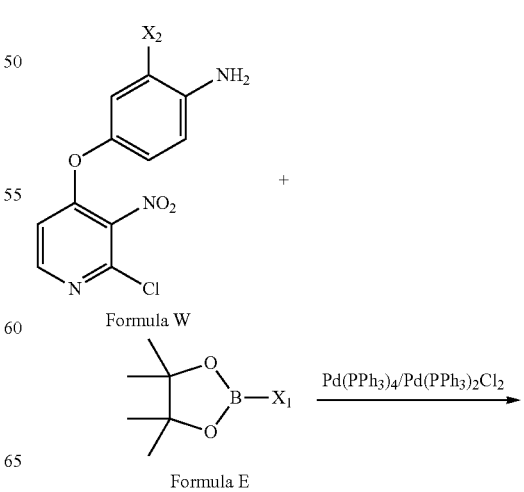

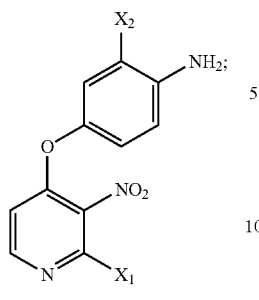

Formula J

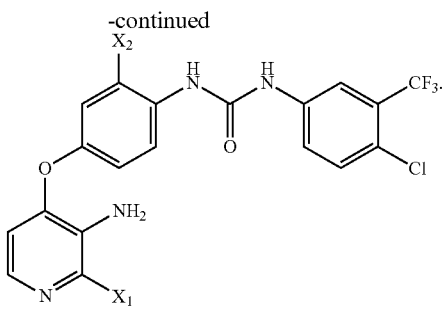

Formula L wherein in the present invention, LDA represents lithium diisopropylamide; THF represents tetrahydrofuran; −78 deg represents −78° C.; DMSO represents dimethyl sulfoxide; rt represents room temperature; DCM represents dichloromethane; conc. represents "concentrated"; TEA represents triethylamine.

3) hydrogenating the compound of Formula J in the presence of palladium-carbon as a catalyst, to get a compound of Formula K:

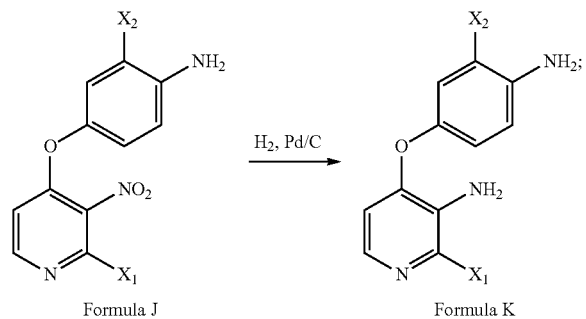

and 4) as shown in the following scheme, reacting the compound of Formula K with a compound of Formula G, to get a compound of Formula L:

The present invention also relates to use of said polysubstituted pyridine compound, or a hydrate, a solvate or a pharmaceutically acceptable salt thereof according to the present invention in preparation of a medicament for treatment and/or prevention of a disease associated with VEGFR-2 (vascular endothelial growth factor receptor-2), VEGFR-3 (vascular endothelial growth factor receptor-3), CRAF (human C-Raf proto-oncogene serine/threonine protein kinase), PDGFR-β (platelet-derived growth factor receptor β), BRAF (human serine/threonine protein kinase), BRAF V600E, KIT and/or FLT-3 (FMS-like tyrosine kinase 3) kinase.

In an embodiment of the present invention, said disease associated with VEGFR-2, VEGFR-3, CRAF, PDGFR-β, BRAF, V600E BRAF, KIT and/or FLT-3 kinase includes tumor or cancer.

Preferably, said tumor or cancer is melanoma, liver cancer, renal carcinoma, acute leukemia, chronic leukemia, non-small cell lung cancer, prostatic cancer, thyroid cancer, skin cancer, colon cancer, rectal cancer, pancreatic cancer, ovarian cancer, mammary cancer, myelodysplastic syndromes, esophageal cancer, or mesothelioma.

The present invention also provides a method for treatment and/or prevention of a disease associated with VEGFR-2, VEGFR-3, CRAF, PDGFR-β, BRAF, V600E BRAF, KIT and/or FLT-3 kinase, comprising administering to a subject in need thereof a therapeutically or prophylactically effective amount of said polysubstituted pyridine compound, or a hydrate, a solvate or a pharmaceutically acceptable salt thereof according to the present invention.

In an embodiment of the present invention, said disease associated with VEGFR-2, VEGFR-3, CRAF, PDGFR-β, BRAF, V600E BRAF, KIT and/or FLT-3 kinase includes tumor or cancer.

Preferably, said tumor or cancer is melanoma, liver cancer, renal carcinoma, acute leukemia, chronic leukemia, non-small cell lung cancer, prostatic cancer, thyroid cancer, skin cancer, colon cancer, rectal cancer, pancreatic cancer, ovarian cancer, mammary cancer, myelodysplastic syndromes, esophageal cancer, or mesothelioma.

The invention also relates to said polysubstituted pyridine compound, or a hydrate, a solvate or a pharmaceutically acceptable salt thereof according to the present invention, for use in treatment and/or prevention of a disease associated with VEGFR-2, VEGFR-3, CRAF, PDGFR-β, BRAF, V600E BRAF, KIT and/or FLT-3 kinase.

In an embodiment of the present invention, said disease associated with VEGFR-2, VEGFR-3, CRAF, PDGFR-β, BRAF, V600E BRAF, KIT and/or FLT-3 kinase includes tumor or cancer.

Preferably, said tumor or cancer is melanoma, liver cancer, renal carcinoma, acute leukemia, chronic leukemia, non-small cell lung cancer, prostatic cancer, thyroid cancer, skin cancer, colon cancer, rectal cancer, pancreatic cancer, ovarian cancer, mammary cancer, myelodysplastic syndromes, esophageal cancer, or mesothelioma.

The present invention also provides a method for inhibiting activity of VEGFR-2, VEGFR-3, CRAF, PDGFR-β, BRAF, V600E BRAF, KIT and/or FLT-3 kinase in a cell, comprising administering to said cell an effective amount of said polysubstituted pyridine compound, or a hydrate, a solvate or a pharmaceutically acceptable salt thereof according to the present invention.

Preferably, said method is carried out in vitro.

Preferably, said method is carried out in vivo.

Preferably, said cell is a cell line, or a cell from a subject, such as a tumor cell or cancer cell.

Preferably, said tumor or cancer is selected from a group consisting of melanoma, liver cancer, renal carcinoma, acute leukemia, chronic leukemia, non-small cell lung cancer, prostatic cancer, thyroid cancer, skin cancer, colon cancer, rectal cancer, pancreatic cancer, ovarian cancer, mammary cancer, myelodysplastic syndromes, esophageal cancer, and mesothelioma.

The present invention also relates to use of said polysubstituted pyridine compound, or a hydrate, a solvate or a pharmaceutically acceptable salt thereof according to the present invention in preparation of an agent, wherein said agent is used for inhibiting activity of VEGFR-2, VEGFR-3, CRAF, PDGFR-β, BRAF, V600E BRAF, KIT and/or FLT-3 kinase in a cell.

Preferably, said agent is used in an in vitro method.

Preferably, said agent is used in an in vivo method.

Preferably, said cell is a cell line, or a cell from a subject, such as a tumor cell or cancer cell.

Preferably, said tumor or cancer is selected from a group consisting of melanoma, liver cancer, renal carcinoma, acute leukemia, chronic leukemia, non-small cell lung cancer, prostatic cancer, thyroid cancer, skin cancer, colon cancer, rectal cancer, pancreatic cancer, ovarian cancer, mammary cancer, myelodysplastic syndromes, esophageal cancer, and mesothelioma.

The present invention also relates to said polysubstituted pyridine compound, or a hydrate, a solvate or a pharmaceutically acceptable salt thereof according to the present invention, for use in inhibiting activity of VEGFR-2, VEGFR-3, CRAF, PDGFR-β, BRAF, V600E BRAF, KIT and/or FLT-3 kinase in a cell.

Preferably, for use in an in vitro method.

Preferably, for use in an in vivo method.

Preferably, said cell is a cell line, or a cell from a subject, such as a tumor cell or cancer cell.

Preferably, said tumor or cancer is selected from a group consisting of melanoma, liver cancer, renal carcinoma, acute leukemia, chronic leukemia, non-small cell lung cancer, prostatic cancer, thyroid cancer, skin cancer, colon cancer, rectal cancer, pancreatic cancer, ovarian cancer, mammary cancer, myelodysplastic syndromes, esophageal cancer, and mesothelioma.

The present invention also provides a kit for inhibiting activity of VEGFR-2, VEGFR-3, CRAF, PDGFR-β, BRAF, V600E BRAF, KIT and/or FLT-3 kinase in a cell, comprising said polysubstituted pyridine compound, or a hydrate, a solvate or a pharmaceutically acceptable salt thereof according to the present invention, and optionally instructions.

In an embodiment of the present invention, said disease associated with VEGFR-2, VEGFR-3, CRAF, PDGFR-β, BRAF, V600E BRAF, KIT and/or FLT-3 kinase includes tumor or cancer.

Preferably, said tumor or cancer is melanoma, liver cancer, renal carcinoma, acute leukemia, chronic leukemia, non-small cell lung cancer, prostatic cancer, thyroid cancer, skin cancer, colon cancer, rectal cancer, pancreatic cancer, ovarian cancer, mammary cancer, myelodysplastic syndromes, esophageal cancer, or mesothelioma.

The present invention also provides a pharmaceutical composition, comprising said polysubstituted pyridine compound, or a hydrate, a solvate or a pharmaceutically acceptable salt thereof according to present invention, and a pharmaceutically acceptable adjuvant (such as carrier or excipient).

Preferably, said pharmaceutical composition is an injection, an oral formulation, a cutaneous permeable agent or a suppository.

Preferably, said pharmaceutical composition is used for the treatment and/or prevention of a disease associated with VEGFR-2, VEGFR-3, CRAF, PDGFR-β, BRAF, V600E BRAF, KIT and/or FLT-3 kinase.

In the present invention, said $C_1$-$C_4$alkyl is selected from a group consisting of methyl, ethyl, n-propyl, isopropyl, n-butyl, isobutyl, sec-butyl, and tert-butyl.

In the present invention, said $C_1$-$C_4$alkoxyl refers to $C_1$-$C_4$alkyl-O—, wherein $C_1$-$C_4$alkyl has the same meanings as defined above.

In the present invention, said halogen is selected from F, Cl, Br, and I.

In the present invention, said $C_1$-$C_2$alkyl refers to methyl or ethyl.

In the present invention, said $C_1$-$C_2$alkoxyl refers to methoxyl or ethoxyl.

If the name of a compound used herein is not consistent with its chemical formula, the chemical formula shall prevail or a person skilled in the art shall determine it according to the practical conditions in combination with the common knowledge.

Some compounds according to the present invention may be crystallized or re-crystallized with water or various organic solvents, and form various solvates in this case. The present invention comprises the stoichiometric solvates including hydrates, also comprises compounds containing a variable amount of water, which are formed when prepared by sublimation under low pressure.

According to the present invention, since the compound of Formula I is used for pharmaceutical purpose, it can be understood that the compound is most preferably provided in a pure form, e.g., with a purity of at least 60%, more suitably a purity of 75%, more preferably a purity of 85%, and most preferably a purity of at least 98% ("%" refers to percentage by weight). The impure compound may be used for the preparation of purer forms used in a pharmaceutical composition. The impure products contain at least 1%, more suitably 5%, more preferably 10% of the compound of Formula I or a pharmaceutically acceptable derivative thereof.

The present invention further relates to a pharmaceutical composition, comprising at least one compound of Formula I and at least one pharmaceutically acceptable carrier or excipient. The compound of Formula I or a pharmaceutically acceptable salt thereof can be used alone, or in combination with a pharmaceutically acceptable carrier or excipient in a form of a pharmaceutical composition. When the compound is used in the form of a pharmaceutical composition, a suitable administration form or dosage form is generally prepared from an effective amount of the compound of Formula I, or a pharmaceutically acceptable salt or a solvate thereof according to the present invention, and one or more pharmaceutically acceptable carriers or excipients. The process involves mixing, granulating, compressing or dissolving the components by suitable means.

The pharmaceutical composition according to the present invention may be administered by any of the following means: oral administration, spray inhalation, rectal administration, intranasal administration, vaginal administration, topical administration, parenteral administration such as subcutaneous, intravenous, intramuscular, intraperitoneal, intrathecal, intraventricular, intrasternal or intracranial injection or input, or administration by virtue of an explant reservoir, among which oral administration, muscular injection, intraperitoneal administration, or intravenous administration is preferred.

The pharmaceutically acceptable carrier comprised in the pharmaceutical composition of the present invention includes, but is not limited to, ion exchanger, aluminum oxide, aluminum stearate, lecithin, serum protein such as human serum protein; buffer substance such as phosphate, glycerol, sorbic acid, potassium sorbate, a partial glyceride mixture of saturated vegetable fatty acid, water, salt, or electrolyte, such as protamine sulfate, di sodium hydrogen phosphate, potassium hydrogen phosphate, sodium chloride, zinc salt, colloided silica, magnesium trisilicate, polyvinylpyrrolidone, cellulose substance, polyethylene glycol, carboxymethylcellulose sodium, polyacrylic ester, beewax, lanocerin and the like. In a pharmaceutical composition, the carrier is present in an amount of 1%~98% by weight, generally of about 80% by weight. For the convenience of use, a local anesthetic, a preservative, a buffer and the like may be directly dissolved in the carrier.

Oral formulations such as oral tablets and capsules may contain excipients, e.g., binders such as syrup, arabic gum, sorbitol, tragacanth or polyvinylpyrrolidone; fillers such as lactose, sucrose, corn starch, calcium phosphate, sorbitol or aminoacetic acid; lubricants such as magnesium stearate, talc, polyethylene glycol or silica; disintegrants such as potato starch; or acceptable lubrication-enhancing agents such as sodium lauryl sulfate. The tablet may be coated by methods well known in pharmaceutics.

The pharmaceutical composition of the present invention in an oral liquid form may be prepared into a suspension of water and oil, a solution, an emulsion, a syrup or an elixir, or into a dry product which is supplemented with water or other suitable medium prior to use. The liquid formulation may contain conventional additives, e.g., suspending agent such as sorbitol, methyl cellulose, glucose syrup, gel, hydroxyethyl cellulose, carboxymethyl cellulose, aluminum stearate gel or hydrogenated edible fat; emulsifier such as lecithin, sorbitan monooleate or gum arabic; or non-aqueous carrier (which may comprise edible oil) such as almond oil, fat such as glycerol, ethylene glycol or ethanol; preservative such as methyl or propyl parahydroxybenzoate, sorbic acid. If necessary, a flavoring agent or a coloring agent may be added. Suppositories may contain conventional suppository bases, such as cocoa butter or other glycerides. For parenteral administration, a liquid dosage form is generally made from a compound and at least one sterilized or aseptic carrier. The carrier is optimally water. Depending on the selected carrier and the concentration of a medicament, the compound may be dissolved in the carrier or be prepared into a suspension solution. When preparing a solution for use in injection, the compound is dissolved in water first, and is packaged into a seal bottle or an ampoule after filtration and sterilization. When topically administered to skin, the compound according to the present invention may be prepared in a suitable form of ointment, lotion or cream, wherein the active ingredient is suspended or dissolved in one or more carriers. The carrier for use in ointment preparations includes, but is not limited to: mineral oil, liquid paraffin, albolene, propylene glycol, polyoxyethylene, polyoxypropylene, emulsifying wax and water. The carrier for use in lotions and creams includes, but is not limited to: mineral oil, sorbitan monostearate, Tween 60, hexadecylester wax, hexadecane aromatic alcohol, 2-octyl dodecanol, benzyl alcohol and water. According to the route of administration, the composition may contain an active ingredient in an amount of 0.1% by weight, or more suitably 10-60% by weight. However, when the composition is in a unit dosage form, each unit preferably contains 50~500 mg active ingredient. Based on the route and the frequency of administration, a therapeutic dose suitable for an adult, for example, is 100-3000 mg per day, such as 1500 mg per day.

It must be realized that the optimal administration dose and interval of the compound of Formula I depend on the conditions such as the severity of a disease or disorder, the properties of the compound, form of administration, route of administration and site of administration as well as the specific mammal to be treated. The optimal administration dose can be determined by a physician.

The polysubstituted pyridine compounds according to the present invention have the following advantages and positive effects over the prior art:

The invention provides a new class of polysubstituted pyridine compounds for the first time. As compared to the existing compounds (such as Sorafenib, or compounds disclosed in CN1341098A or CN102532113A), polysubstituted pyridine compounds of Formula I according to the present invention have better anti-tumor effect, and can inhibit various kinases in a cell and at cell surface simultaneously, including vascular endothelial growth factor receptor-2 (VEGFR-2), vascular endothelial growth factor receptor-3 (VEGFR-3), CRAF, platelet-derived growth factor receptor-β(PDGFR-β), BRAF, V600E BRAF, KIT and FLT-3 kinase. Particularly, some preferred compounds according to the present invention have dual anti-tumor effects. On one hand, they can block the angiogenesis of tumor by inhibiting VEGFR and PDGFR, and thereby inhibit the growth of tumor cells; on the other hand, they can inhibit tumor growth by inhibiting RAF/MEK/ERK signal transduction pathway, resulting in more effective anti-tumor effects.

In addition, the compounds according to the present invention have not only significantly excellent anti-tumor effect, but also significantly excellent pharmacokinetic characteristics, are obviously superior to the commercially available drug Sorafenib in terms of data such as blood concentration in vivo, and are very suitable for oral and intravenous administration.

In order to obtain more effective anti-tumor drugs, the inventors performed a large number of screening tests. For example, the inventors screened at the position of the substituents X3, X4 and X5 on the pyridine ring of Formula II by pharmacodynamic experiments.

Formula II

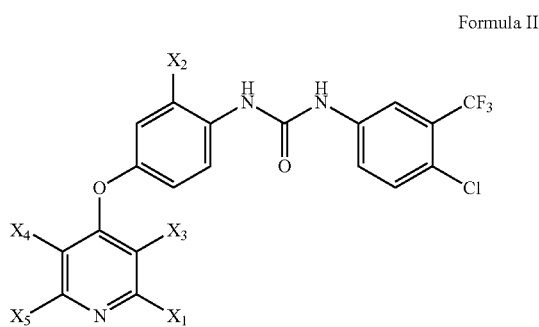

The inventors found surprisingly by pharmacodynamic experiments that when both $X_4$ and $X_5$ in the pyridine ring were hydrogen, and $X_3$ was substituted by a substituent, due to electron cloud effect and a change in the steric configuration of the compound molecule, the interaction of pharmacophoric group 2-(1-methyl-4-pyrazolyl) or 2-(methyl-carbamoyl) with the nitrogen atom on the pyridine ring was enhanced, resulting in a higher binding strength between the compound molecule and the receptor. Moreover, the inventors also found surprisingly through a lot of experimentations that when $X_3$ was hydrogen in the pyridine ring, the position of $X_3$ was a site at which the compound can be easily metabolized; when $X_3$ of Formula I was substituted by a substituent, the substituent blocked the site, thereby enhanced the metabolic stability of the compound and ensured a high blood concentration of the compound in vivo, which further enhanced the efficacy of the compound according to the present invention. Based on these discoveries, the inventors further arrived at the technical solutions of the present invention. The compounds according to the present invention have significantly excellent anti-tumor effects, and are significantly superior to the compounds disclosed in Chinese Patent Application Documents CN1341098, CN201110435847.9, as well as the commercially available drug Sorafenib.

The inventors further found by pharmacodynamic experiments that when $X_3$ was an electron withdrawing group, the compounds according to the present invention had better therapeutic effect. The preferred electron withdrawing group is F, Cl or cyano.

A significant difference between the technical solutions of the present invention and the technical solutions of the patent application CN201110435847.9 as filed previously by the inventors is: the compounds according to the present invention are substituted at position 3 of the pyridine ring (i.e., X3 of Formula I according to the present invention), while the compounds disclosed in CN201110435847.9 are not substituted at positions 3, 5 and 6 of the pyridine ring (i.e., X3, X4 and X5 of Formula II in the instant specification).

Also, the commercially available anti-tumor drug Sorafenib is not substituted at positions 3, 5 and 6 of the pyridine ring (i.e., X3, X4, X5 of Formula II according to the present invention), thus the compounds according to the present invention are also structurally different from the compound Sorafenib.

The inventors found by pharmacodynamic comparative experiments that the compounds according to the present invention had significantly better anti-tumor effects than the compounds disclosed in CN1341098, CN201110435847.9, which were not substituted at positions 3, 5 and 6 of the pyridine ring (i.e., X3, X4 and X5 of Formula II in the specification according to the present invention). Moreover, the compounds according to the present invention are also significantly superior to the commercially available anti-tumor drug Sorafenib, which indicates that compared to the commercially available anti-tumor drug Sorafenib, the compounds according to the present invention are more effective anti-tumor compounds capable of inhibiting multiple kinases.

The compounds according to the present invention have not only significantly excellent anti-tumor effect, but also significantly excellent pharmacokinetic characteristics, are obviously superior to the commercially available drug Sorafenib in terms of data such as blood concentration in vivo, and are very suitable for oral and intravenous administration.

DESCRIPTION OF THE DRAWINGS

FIG. 1 illustrates the half maximal inhibitory concentration of compounds of Example 1, Example 2, Comparative example 3, Comparative example 4, Comparative example 5, and Sorafenib free base on the kinase VEGFR2.

The corresponding relationship between the compounds in the drawings and the Examples is as follows:

| Compound in the drawings | Corresponding example |
| --- | --- |
| FD-2013015 | Example 1 |
| FD-2013018 | Example 2 |
| FD-2013016 | Comparative example 3 |
| FD-2013019 | Comparative example 4 |
| FD-2013017 | Comparative example 5 |

SPECIFIC MODES FOR CARRYING OUT THE INVENTION

The invention is further described, but is not restricted by the following embodiments and reference to the drawings. Based on the basic thought of the present invention, a person skilled in the art can make various modifications or improvements. These modifications or improvements fall into the scope of the invention as long as they do not depart from the basic thought of the present invention.

In the following examples, except otherwise specified, all the reagents are commercially available, for example from J&K SCIENTIFIC Co. Ltd., Alfa Aesar (Tianjin) Chemical Co. Ltd., or Beijing Ouhe Technology Co., Ltd.

In following examples, the calculation formula of yield is:

yield=weight of product×molar mass of raw material/(weight of raw material×molar mass of product).

Example 1

FD-2013015

1-(4-chloro-3-(trifluoromethyl)phenyl)-3-(4-(3-fluoro-2-(1-methyl-4-pyrazolyl)-pyridin-4-yl-oxy)phenyl)urea

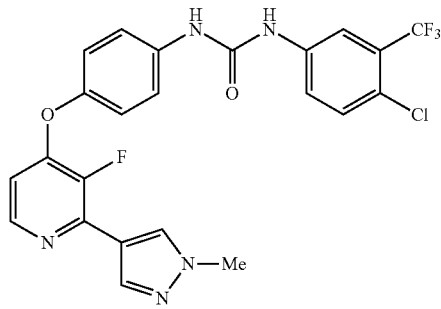 [SMILES: Cn1cc(-c2nccc(Oc3ccc(NC(=O)Nc4ccc(Cl)c(C(F)(F)F)c4)cc3)c2Cl)cn1]

Preparation Method

Step 1: Synthesis of 2-chloro-3-fluoro-4-chloropyridine

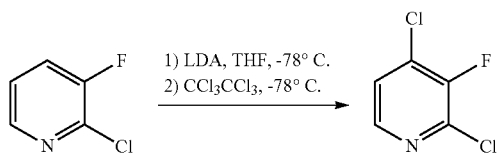

In an atmosphere of nitrogen gas, at −30° C., n-butyl lithium (2.4M hexane solution, 13.13 mL, 31.5 mmol) was added dropwise into a solution of diisopropylamine (3.18 g, 31.5 mmol) in anhydrous tetrahydrofuran (30 mL) to get a reaction mixture. The reaction mixture was stirred at −30° C. for 30 minutes, and then cooled to −78° C. A solution of 2-chloro-3-fluoropyridine (3.95 g, 30 mmol) in anhydrous tetrahydrofuran (20 mL) was added dropwise, and the reaction mixture was then stirred at −78° C. for 60 minutes. A solution of hexachloroethane (7.10 g, 30 mmol) in anhydrous tetrahydrofuran (50 mL) was added dropwise, and the reaction mixture was then stirred at −78° C. for 60 minutes. The reaction mixture was quenched with saturated ammonium chloride solution (50 mL), diluted with water (50 mL), and extracted with ethyl acetate (100 mL×3). The organic phases were combined. The combined organic phases were washed with saline solution (100 mL×3), dried with anhydrous sodium sulfate, filtrated, and concentrated. The residue was purified by column chromatography (petroleum ether:ethyl acetate=100:1) to get product as yellow solid (3.60 g, yield: 72%).

$^1$H NMR (300 MHz, CDCl$_3$): 8.14 (d, J=5.1 Hz, 1H), 7.34 (t, J=5.1 Hz, 1H)

MS (ESI+): m/z 166.2 [M+H]$^+$

Step 2: Synthesis of 2-chloro-3-fluoro-4-(4-aminophenoxy)pyridine

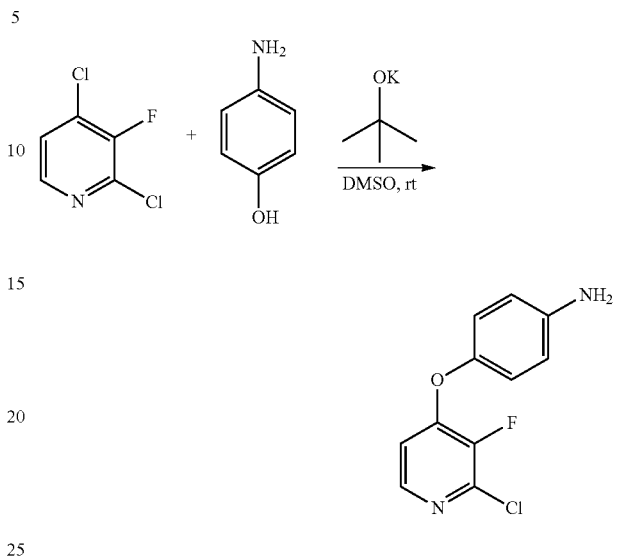

A solution of 4-aminophenol (24.8 g, 227 mmol) in anhydrous dimethyl sulfoxide (210 mL) was bubbled with nitrogen gas for 10 minutes, and potassium tert-butoxide (26.80 g, 238.8 mmol) was then added to get a reaction mixture. The reaction mixture was stirred at room temperature for 30 minutes, and then 2-chloro-3-fluoro-4-chloropyridine (37.68 g, 227 mmol) was added. The reaction mixture was stirred at room temperature for 5 h, and then diluted with water (1000 mL) and extracted with ethyl acetate (500 mL×3). The organic phases were combined. The combined organic phases were washed with saline solution (500 mL×2), dried with anhydrous sodium sulfate, filtrated, and concentrated. The residue was purified by column chromatography (silica gel, petroleum ether:ethyl acetate=5:1, v/v) to get product as light yellow solid (15.0 g, yield: 28%).

$^1$H NMR (300 MHz, DMSO-d$_6$): δ 5.22 (br s, 2H), 6.62 (d, J=9.0 Hz, 2H), 6.75 (t, J=5.7 Hz, 1H), 6.92 (d, J=9.0 Hz, 2H), 8.05 (d, J=5.7 Hz, 1H)

MS (ESI+): m/z 239.1 [M+H]$^+$

Step 3: Synthesis of 4-(3-fluoro-2-(1-methyl-4-pyrazolyl)-pyridin-4-yl-oxy)aniline

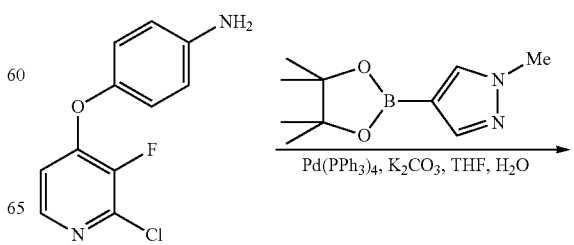

-continued

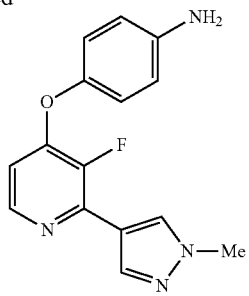

A mixture of 2-chloro-3-fluoro-4-(4-aminophenoxy)pyridine (7.2 g, 30.2 mmol), 1-methylpyrazol-4-yl-boronic acid pinacol ester (6.3 g, 30.2 mmol), potassium carbonate (12.5 g, 90.6 mmol) and tetrakis (triphenylphosphine) palladium (1.74 g, 1.5 mmol) in tetrahydrofuran (THF, 180 mL) and water (30 mL) was bubbled with argon gas for 5 minutes, and then stirred in an atmosphere of argon gas at 85° C. for 24 hours to get a reaction mixture. The reaction mixture was diluted with water (100 mL), and extracted with ethyl acetate (100 mL×3). The organic phases were combined. The combined organic phases were washed with saline solution (100 mL×2), dried with anhydrous sodium sulfate, filtrated, and concentrated. The residue was purified by column chromatography (silica gel, petroleum ether:ethyl acetate=1:2, v/v) to get product as light yellow solid (5.4 g, yield: 60%).

$^1$H NMR (300 MHz, DMSO-d$_6$): δ 3.93 (s, 3H), 5.18 (br s, 2H), 6.54 (t, J=5.7 Hz, 1H), 6.63 (d, J=8.7 Hz, 2H), 6.91 (d, J=8.7 Hz, 2H), 7.98 (d, J=0.6 Hz, 1H), 8.15 (d, J=5.4 Hz, 1H), 8.29 (d, J=2.1 Hz, 1H)

MS (ESI+): m/z 285.1 [M+H]$^+$

Step 4: Synthesis of 1-(4-chloro-3-(trifluoromethyl) phenyl)-3-(4-(3-fluoro-2-(1-methyl-pyrazol-4-yl)-pyridin-4-yl-oxy)phenyl)urea

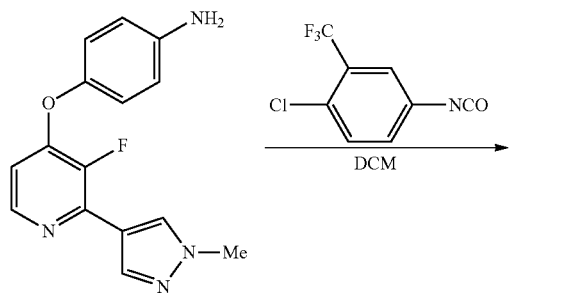

A mixed solution of 4-(3-fluoro-2-(1-methyl-pyrazol-4-yl)-pyridin-4-yl-oxy)aniline (1.71 g, 6.0 mmol) and 4-chloro-3-trifluoromethylphenyl isocyanate (1.6 g, 7.2 mmol) in dichloromethane (30 mL) was stirred at room temperature for 12 hours, and then filtrated, white solid was collected, washed with dichloromethane, and dried to get product as white solid (2.35 g, yield: 75%).

$^1$H NMR (300 MHz, DMSO-d$_6$): δ 3.93 (s, 3H), 6.66 (t, J=6.0 Hz, 1H), 7.18 (d, J=9.0 Hz, 2H), 7.56 (d, J=9.0 Hz, 2H), 7.59-7.63 (m, 2H), 7.98 (s, 1H), 8.10 (d, J=1.8 Hz, 1H), 8.20 (d, J=5.4 Hz, 1H), 8.30 (d, J=1.8 Hz, 1H), 8.98 (s, 1H), 9.18 (s, 1H)

MS (ESI+): m/z 505.8 [M+H]$^+$

Step 5: Synthesis of 1-(4-chloro-3-(trifluoromethyl) phenyl)-3-(4-(3-fluoro-2-(1-methyl-pyrazol-4-yl)-pyridin-4-yl-oxy)phenyl)urea p-toluene sulfonate

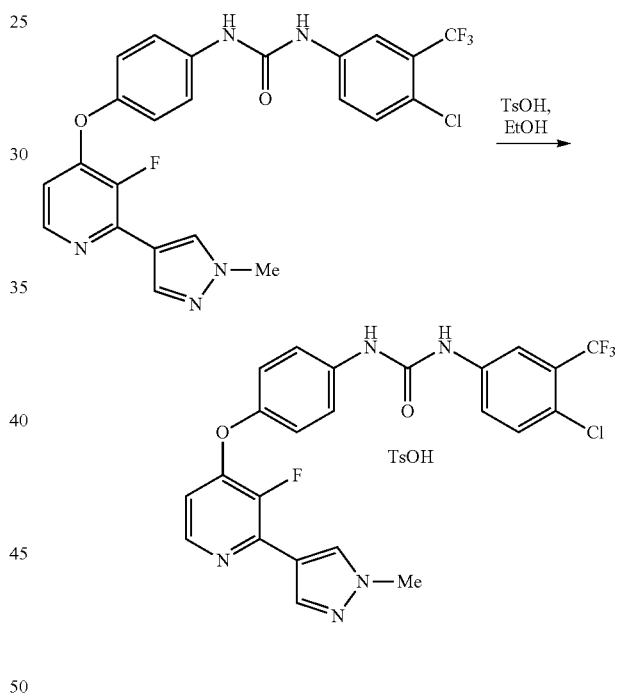

A mixture of 1-(4-chloro-3-(trifluoromethyl)phenyl)-3-(4-(3-fluoro-2-(1-methyl-pyrazol-4-yl)-pyridin-4-yl-oxy) phenyl)urea (1.518 g, 3 mmol) and p-toluenesulfonic acid monohydrate (0.684 g, 3.6 mmol) in anhydrous ethanol (20 mL) was heated to reflux, and anhydrous ethanol was further added until solid was dissolved completely. The resultant clear solution was filtered and the filtrate was standing overnight, and then filtrated under suction, the resultant white solid was collected, and dried to get product as white solid (1.328 g, yield: 65%).

$^1$H NMR (300 MHz, DMSO-d$_6$) δ 9.32 (s, 1H), 9.12 (s, 1H), 8.39 (d, J=1.2 Hz, 1H), 8.28 (d, J=5.7 Hz, 1H), 8.13 (d, J=2.4 Hz, 1H), 8.06 (s, 1H), 7.72-7.56 (m, 4H), 7.51 (d, J=8.0 Hz, 2H), 7.23 (d, J=9.0 Hz, 2H), 7.13 (d, J=8.1 Hz, 2H), 6.77 (t, J=6.2 Hz, 1H), 3.95 (s, 3H), 2.29 (s, 3H).

Example 2

FD-2013018

1-(4-chloro-3-(trifluoromethyl)phenyl)-3-(4-(3-chloro-2-(1-methyl-pyrazol-4-yl)-pyridin-4-yl-oxy)phenyl)urea

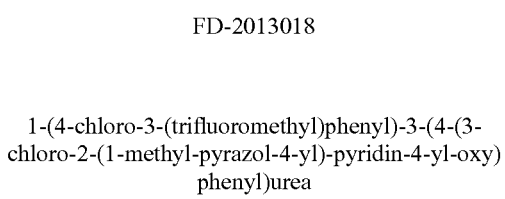

Preparation Method

Step 1: Synthesis of 2,3-dichloro-4-iodopyridine

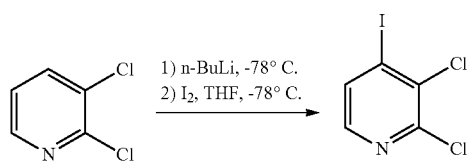 [SMILES: Clc1cccnc1Cl ; Clc1nccc(I)c1Cl]

In an atmosphere of argon gas, at −78° C., n-butyl lithium (2.4M hexane solution, 59.12 mL, 141.9 mmol) was added dropwise to a solution of 2,3-dichloropyridine (20 g, 135.1 mmol) in anhydrous tetrahydrofuran (350 mL) to get a reaction mixture, and the reaction mixture was stirred at −78° C. for 90 minutes. A solution of iodine (41 g, 161.5 mmol) in anhydrous tetrahydrofuran (100 mL) was added dropwise, and the reaction mixture was stirred at −78° C. for 60 minutes. The temperature was then increased to room temperature. The reaction mixture was quenched with saturated ammonium chloride solution (100 mL), diluted with water (100 mL), and extracted with ethyl acetate (200 mL×3). The organic phases were combined. The combined organic phases were washed with saline solution (200 mL×2), dried with anhydrous sodium sulfate, filtrated, and concentrated. The residue was purified by column chromatography (silica gel, petroleum ether:ethyl acetate=100:1) to get product as yellow solid (31.5 g, yield: 85.1%).

$^1$H NMR (300 MHz, DMSO-$d_6$): 8.08 (d, J=5.4 Hz, 1H), 8.65 (d, J=5.4 Hz, 1H)

MS (ESI+): m/z 273.9 [M+H]$^+$

Step 2: Synthesis of 2,3-dichloro-4-(4-aminophenoxy)pyridine

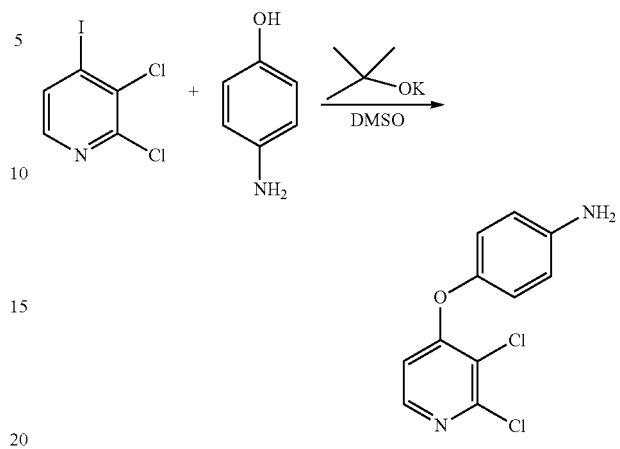

A solution of 4-aminophenol (13.85 g, 127.0 mmol) in anhydrous dimethyl sulfoxide (120 mL) was bubbled with nitrogen gas for 10 minutes, and potassium tert-butoxide (13.60 g, 121.2 mmol) was then added to get a reaction mixture. The reaction mixture was stirred at room temperature for 30 minutes, and then 2,3-dichloro-4-iodopyridine (31.5 g, 115.4 mmol) was added. The reaction mixture was stirred at room temperature for 5 hours, and then diluted with water (500 mL) and extracted with ethyl acetate (300 mL×3). The organic phases were combined. The combined organic phases were washed with saline solution (300 mL×2), dried with anhydrous sodium sulfate, filtrated, and concentrated. The residue was purified by column chromatography (silica gel, petroleum ether:ethyl acetate=4:1, v/v) to get product as light yellow solid (27.5 g, yield: 93.7%).

$^1$H NMR (400 MHz, DMSO-$d_6$): δ 5.24 (br s, 2H), 6.64 (d, J=8.8 Hz, 2H), 6.67 (d, J=5.6 Hz, 1H), 6.90 (d, J=8.8 Hz, 2H), 8.39 (d, J=5.6 Hz, 1H)

MS (ESI+): m/z 255.0 [M+H]$^+$

Step 3: Synthesis of 4-(3-chloro-2-(1-methyl-pyrazol-4-yl)-pyridin-4-yl-oxy)aniline

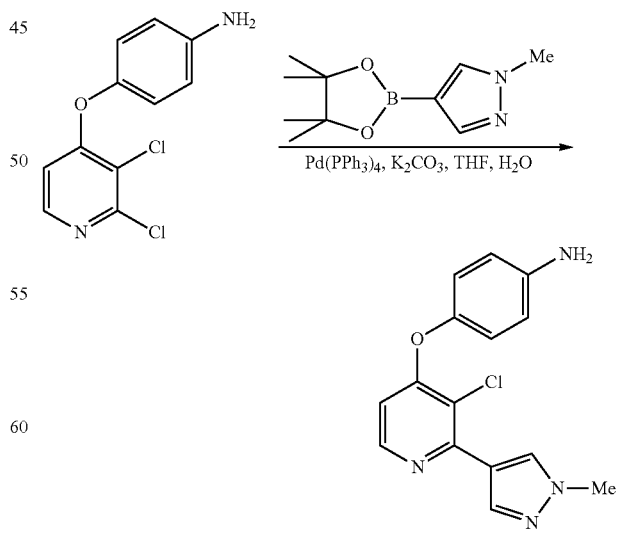

A mixture of 2,3-dichloro-4-(4-aminophenoxy)pyridine (9.1 g, 35.7 mmol), 1-methylpyrazol-4-yl-boronic acid pinacol ester (7.42 g, 35.7 mmol), potassium carbonate (14.76 g, 106.9 mmol) and tetrakis(triphenylphosphine)palladium (2 g, 1.72 mmol) in tetrahydrofuran (THF, 210 mL) and water (35 mL) was bubbled with argon gas for 5 minutes, and then stirred in an atmosphere of argon gas at 85° C. for 24 hours to get a reaction mixture. The reaction mixture was diluted with water (100 mL), and extracted with ethyl acetate (100 mL×3). The organic phases were combined. The combined organic phases were washed with saline solution (100 mL×2), dried with anhydrous sodium sulfate, filtrated, and concentrated. The residue was purified by column chromatography (silica gel, petroleum ether:ethyl acetate=1:2, v/v) to get product as light yellow solid (4.85 g, yield: 45.2%).

$^1$H NMR (400 MHz, DMSO-$d_6$): δ 3.93 (s, 3H), 5.19 (br s, 2H), 6.46 (d, J=5.6 Hz, 1H), 6.64 (d, J=8.8 Hz, 2H), 6.88 (d, J=8.8 Hz, 2H), 8.11 (s, 1H), 8.27 (d, J=5.6 Hz, 1H), 8.48 (s, 1H)

MS (ESI+): m/z 301.0 [M+H]$^+$

Step 4: Synthesis of 1-(4-chloro-3-(trifluoromethyl) phenyl)-3-(4-(3-chloro-2-(1-methyl-pyrazol-4-yl)-pyridin-4-yl-oxy)phenyl)urea

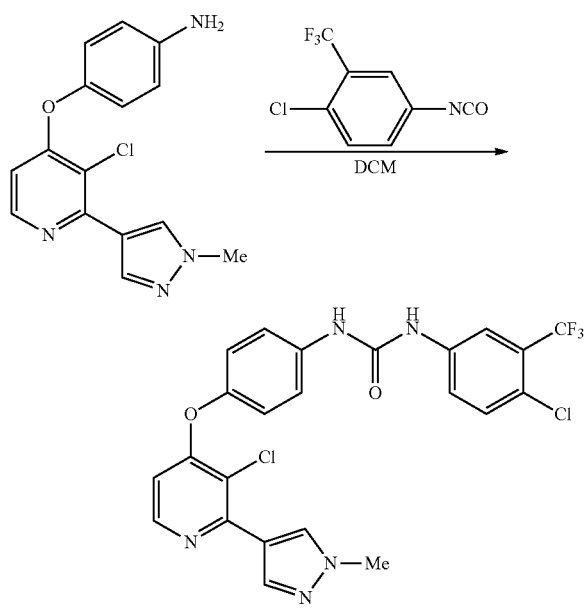

A solution of 4-(3-chloro-2-(1-methyl-pyrazol-4-yl)-pyridin-4-yl-oxy) aniline (4.85 g, 16.1 mmol) and 4-chloro-3-trifluoromethylphenyl isocyanate (4.28 g, 19.3 mmol) in dichloromethane (50 mL) was stirred at room temperature for 12 hours, then filtrated, the resultant white solid was collected, washed with dichloromethane, and dried to get product as white solid (7.2 g, yield: 85.5%).

$^1$H NMR (400 MHz, DMSO-$d_6$): δ 3.94 (s, 3H), 6.56 (d, J=5.2 Hz, 1H), 7.19 (d, J=8.8 Hz, 2H), 7.59 (d, J=8.8 Hz, 2H), 7.61-7.68 (m, 2H), 8.12 (s, 1H), 8.13 (s, 1H), 8.32 (d, J=5.6 Hz, 1H), 8.51 (s, 1H), 9.01 (s, 1H), 9.21 (s, 1H)

MS (ESI+): m/z 522.1 [M+H]$^+$

Step 5: Synthesis of 1-(4-chloro-3-(trifluoromethyl) phenyl)-3-(4-(3-chloro-2-(1-methyl-pyrazol-4-yl)-pyridin-4-yl-oxy)phenyl)urea p-toluene sulfonate

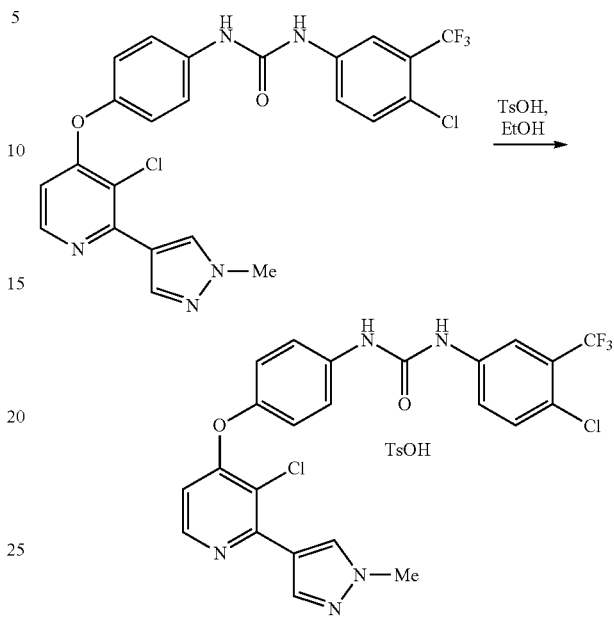

A mixture of 1-(4-chloro-3-(trifluoromethyl)phenyl)-3-(4-(3-chloro-2-(1-methyl-pyrazol-4-yl)-pyridin-4-yl-oxy) phenyl)urea (1.570 g, 3 mmol) and p-toluenesulfonic acid monohydrate (0.684 g, 3.6 mmol) in anhydrous ethanol (20 mL) was heated to reflux, and anhydrous ethanol was added until the solid was completely dissolved. The resultant clear solution was filtrated, the filtrate was standing overnight, and then filtrated under suction, the resultant white solid was collected, and dried to get product as white solid (1.428 g, yield: 69%)

1H NMR (300 MHz, DMSO-$d_6$) δ 9.33 (s, 1H), 9.14 (s, 1H), 8.56 (s, 1H), 8.42-8.32 (dd, J=6.0, 2.4 Hz, 1H), 8.15 (s, 1H), 8.13 (d, J=2.4 Hz, 1H), 7.71-7.58 (m, 4H), 7.50 (d, J=8.0 Hz, 2H), 7.21 (d, J=8.7 Hz, 3H), 7.13 (d, J=7.8 Hz, 2H), 6.71-6.60 (m, 1H), 3.95 (s, 3H), 2.29 (s, 3H).

Example 3

FD-2013024

1-(4-chloro-3-(trifluoromethyl)phenyl)-3-(4-(3-chloro-2-(1-methyl-pyrazol-4-yl)-pyridin-4-yl-oxy)-2-fluorophenyl)urea

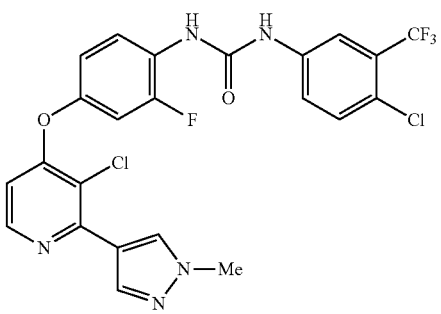 [SMILES: Cn1cc(-c2nccc(Oc3ccc(NC(=O)Nc4ccc(Cl)c(C(F)(F)F)c4)c(F)c3)c2Cl)cn1]

Preparation Method

Step 1: Synthesis of 2,3-dichloro-4-(4-amino-3-fluorophenoxy)pyridine

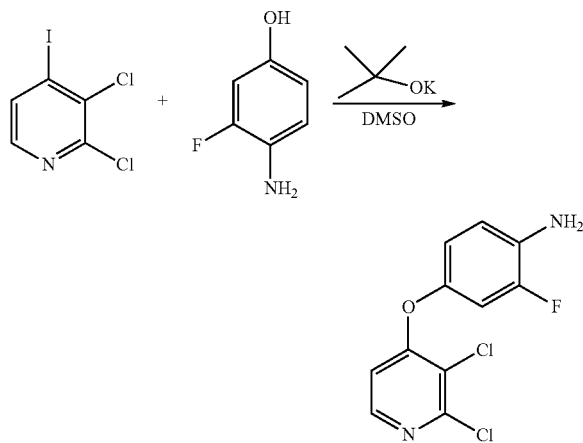

A solution of 4-amino-3-fluorophenol (1.69 g, 13.28 mmol) in anhydrous dimethyl sulfoxide (15 mL) was bubbled with nitrogen gas for 10 minutes, and 2,3-dichloro-4-iodopyridine (3.31 g, 12.13 mmol) was then added to get a reaction mixture. The reaction mixture was stirred at room temperature for 30 minutes, then 2,3-dichloro-4-iodopyridine (31.5 g, 115.4 mmol) was added. The reaction mixture was stirred at room temperature for 5 hours, diluted with water (50 mL) and extracted with ethyl acetate (30 mL×3). The organic phases were combined. The combined organic phases were washed with saline solution (30 mL×2), dried with anhydrous sodium sulfate, filtrated, and concentrated. The residue was purified by column chromatography (silica gel, petroleum ether:ethyl acetate=4:1, v/v) to get product as light yellow solid (1.0 g, yield: 30%).

$^1$H NMR (300 MHz, DMSO-$d_6$) δ 8.17 (d, J=5.6 Hz, 1H), 7.16-7.00 (m, 1H), 6.92-6.78 (m, 2H), 6.75 (d, J=5.6 Hz, 1H), 5.26 (br s, 2H)

MS (ESI+): m/z 272.9 [M+H]$^+$

Step 2: Synthesis of 4-(3-chloro-2-(1-methyl-pyrazol-4-yl)-pyridin-4-yl-oxy)-2-fluoroaniline

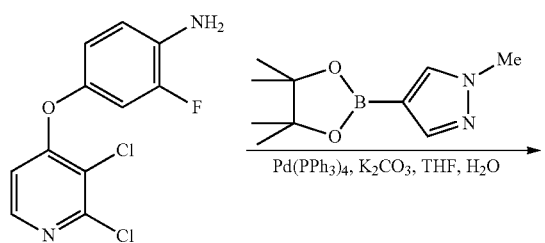

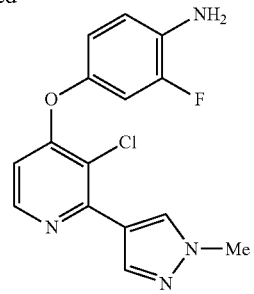

A mixture of 2,3-dichloro-4-(4-amino-3-fluorophenoxy)pyridine (0.40 g, 1.47 mmol), 1-methylpyrazole-4-yl-boronic acid pinacol ester (0.35 g, 1.68 mmol), potassium carbonate (0.70 g, 5.07 mmol) and tetrakis(triphenylphosphine)palladium (0.10 g, 0.086 mmol) in tetrahydrofuran (THF, 5 mL) and water (1 mL) was bubbled with argon gas for 5 minutes, and was stirred in an atmosphere of argon gas at 85° C. for 24 hours to get a reaction mixture. The reaction mixture was diluted with water (20 mL), and extracted with ethyl acetate (20 mL×3). The organic phases were combined. The combined organic phases were washed with saline solution (20 mL×2), dried with anhydrous sodium sulfate, filtrated, and concentrated. The residue was purified by column chromatography (silica gel, petroleum ether:ethyl acetate=1:2, v/v) to get product as light yellow solid (0.23 g, yield: 49%).

$^1$H NMR (300 MHz, DMSO-$d_6$) δ 8.48 (s, 1H), 8.29 (d, J=5.5 Hz, 1H), 8.11 (d, J=0.6 Hz, 1H), 7.04 (dd, J=11.9, 2.3 Hz, 1H), 6.90-6.75 (m, 2H), 6.53 (d, J=5.5 Hz, 1H), 5.21 (s, 2H), 3.93 (s, 3H)

MS (ESI+): m/z 319.0 [M+H]$^+$

Step 3: Synthesis of 1-(4-chloro-3-(trifluoromethyl)phenyl)-3-(4-(3-chloro-2-(1-methyl-pyrazol-4-yl)-pyridin-4-yl-oxy)-2-fluorophenyl)urea

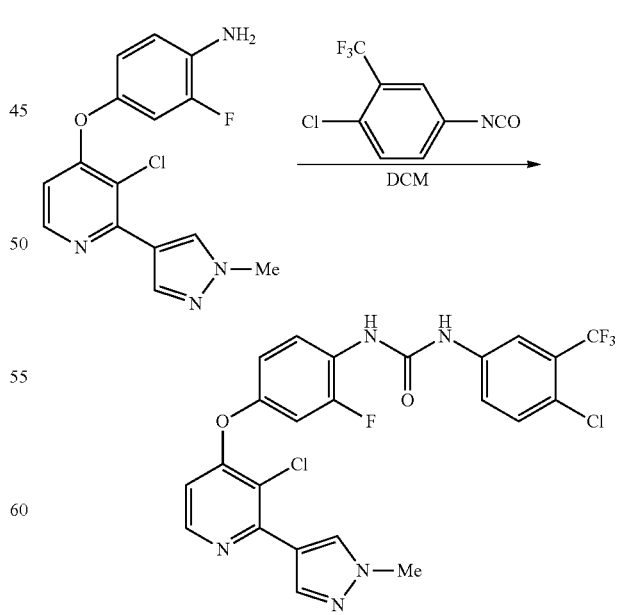

A solution of 4-(3-chloro-2-(1-methyl-pyrazol-4-yl)-pyridin-4-yl-oxy)-2-fluoroaniline (0.23 g, 0.72 mmol) and 4-chloro-3-trifluoromethyl phenyl isocyanate (0.16 g, 0.72 mmol) in dichloromethane (5 mL) was stirred at room temperature for 12 hours, and then filtrated, the resultant white solid was collected, washed with dichloromethane, and dried to get product as white solid (0.30 g, yield: 77%).

¹H NMR (300 MHz, DMSO-d₆) δ 9.52 (s, 1H), 8.75 (s, 1H), 8.52 (s, 1H), 8.36 (d, J=5.5 Hz, 1H), 8.26-8.05 (m, 3H), 7.64 (s, 2H), 7.36 (dd, J=11.5, 2.6 Hz, 1H), 7.07 (d, J=8.1 Hz, 1H), 6.69 (d, J=5.5 Hz, 1H), 3.94 (s, 3H)

MS (ESI+): m/z 540.0 [M+H]⁺

Example 4

FD-2013025

1-(4-chloro-3-(trifluoromethyl)phenyl)-3-(4-(3-cyano-2-(1-methyl-pyrazol-4-yl)-pyridin-4-yl-oxy)phenyl)urea

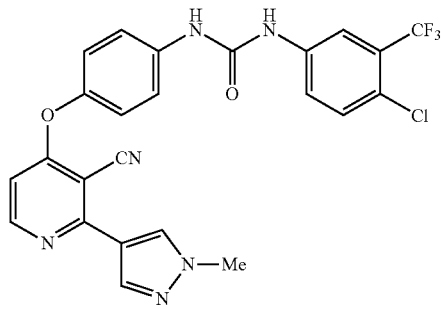 [SMILES: Cn1cc(-c2nccc(Oc3ccc(NC(=O)Nc4ccc(Cl)c(C(F)(F)F)c4)cc3)c2C#N)cn1]

Preparation Method

Step 1: Synthesis of 2-chloro-4-iodonicotinonitrile

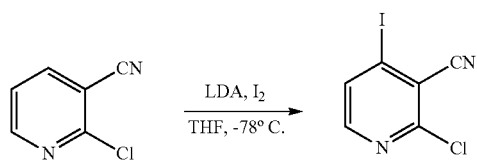 [SMILES: N#Cc1cccnc1Cl ; N#Cc1c(I)ccnc1Cl]

In an atmosphere of argon gas, at −30° C., n-butyl lithium (2.4M hexane solution, 3.0 mL, 7.2 mmol) was added dropwise to a solution of diisopropylamine (0.728 g, 7.2 mmol) in anhydrous tetrahydrofuran (20 mL) to get a reaction mixture. The reaction mixture was stirred at −30° C. for 30 minutes, and then cooled to −78° C. A solution of 2-chloro-nicotinonitrile (1.0 g, 7.2 mmol) in anhydrous tetrahydrofuran (10 mL) was added dropwise, and the reaction mixture was then stirred at −78° C. for 60 minutes. A solution of iodine (1.8 g, 7.2 mmol) in anhydrous tetrahydrofuran (10 mL) was added dropwise, and the reaction mixture was then stirred at −78° C. for 30 minutes. The reaction mixture was quenched with saturated ammonium chloride solution (50 mL), diluted with water (50 mL), and extracted with ethyl acetate (100 mL×3). The organic phases were combined. The combined organic phases were washed with saline solution (100 mL×3), dried with anhydrous sodium sulfate, filtrated, and concentrated. The residue was purified by column chromatography (petroleum ether:ethyl acetate=80:1) to get product as yellow solid (0.357 g, yield: 19%).

¹H NMR (400 MHz, DMSO-d₆) δ 8.32 (d, J=5.2 Hz, 1H), 8.15 (d, J=5.2 Hz, 1H)

MS (ESI+): m/z 264.9 [M+H]⁺

Step 2: Synthesis of 2-chloro-3-cyano-4-(4-aminophenoxy)pyridine

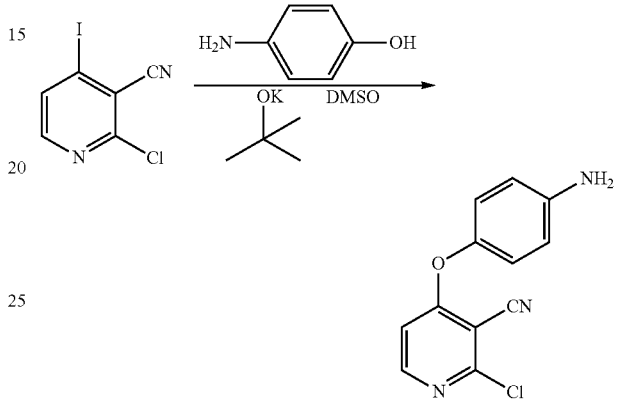

A solution of 4-aminophenol (164 mg, 1.48 mmol) in anhydrous dimethyl sulfoxide (3 mL) was bubbled with nitrogen gas for 10 minutes, and potassium tert-butoxide (166 mg, 1.48 mmol) was then added to get a reaction mixture. The reaction mixture was stirred at room temperature for 30 minutes, 2-chloro-4-iodonicotinonitrile (355 mg, 1.34 mmol) was added. The reaction mixture was stirred at room temperature for 5 hours, and then diluted with water (30 mL) and extracted with ethyl acetate (30 mL×3). The organic phases were combined. The combined organic phases were washed with water (30 mL×2), washed with saline solution (30 mL×2), dried with anhydrous sodium sulfate, filtrated, and concentrated. The residue was purified by column chromatography (silica gel, petroleum ether:ethyl acetate=4:1, v/v) to get product as light yellow solid (210 mg, yield: 61%).

¹H NMR (400 MHz, DMSO-d₆) δ 8.42 (d, J=6.0 Hz, 1H), 6.96 (d, J=8.8 Hz, 2H), 6.76 (d, J=6.0 Hz, 1H), 6.65 (d, J=8.8 Hz, 2H), 5.29 (s, 2H)

MS (ESI+): m/z 246.0 [M+H]⁺

Step 3: Synthesis of 4-(3-cyano-2-(1-methyl-pyrazol-4-yl)-pyridin-4-yl-oxy)aniline

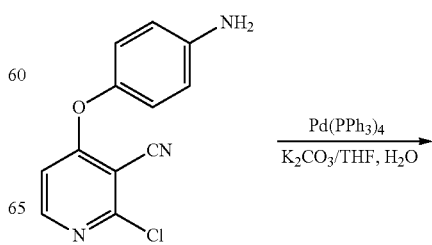

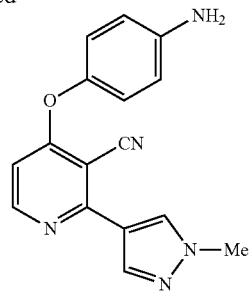

A mixture of 2-chloro-3-cyano-4-(4-aminophenoxy)pyridine (200 mg, 0.816 mmol), 1-methylpyrazol-4-yl-boronic acid pinacol ester (187 mg, 0.878 mmol), potassium carbonate (338 mg, 2.45 mmol) and tetrakis(triphenylphosphine)palladium (95 mg, 0.0816 mmol) in tetrahydrofuran (THF, 6 mL) and water (1 mL) was bubbled with argon gas for 5 minutes, and then stirred in an atmosphere of argon gas at 85° C. for 24 hours to get a reaction mixture. The reaction mixture was diluted with water (20 mL), and extracted with ethyl acetate (20 mL×3). The organic phases were combined. The combined organic phases were washed with water (20 mL×2), washed with saturated saline solution (20 mL×2), dried with anhydrous sodium sulfate, filtrated, and concentrated. The residue was purified by column chromatography (silica gel, petroleum ether:ethyl acetate=1:2, v/v) to get product as light yellow solid (95 mg, yield: 40%).

$^1$H NMR (300 MHz, DMSO-d$_6$) δ 8.52 (d, J=6.0 Hz, 1H), 8.48 (s, 1H), 8.17 (s, 1H), 6.95 (d, J=8.7 Hz, 2H), 6.65 (d, J=8.7 Hz, 2H), 6.51 (d, J=6.0 Hz, 1H), 5.25 (s, 2H), 3.96 (s, 3H)

MS (ESI+): m/z 292.1 [M+H]$^+$

Step 4: Synthesis of 1-(4-chloro-3-(trifluoromethyl)phenyl)-3-(4-(3-cyano-2-(1-methyl-pyrazol-4-yl)-pyridin-4-yl-oxy)phenyl)urea

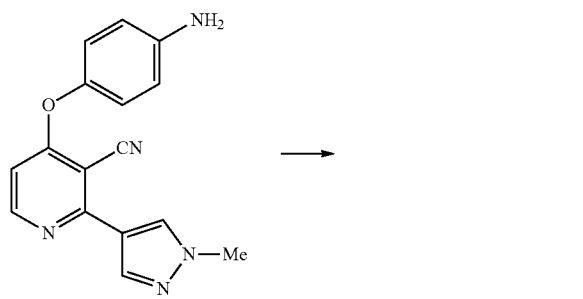

A solution of 4-(3-cyano-2-(1-methyl-pyrazol-4-yl)-pyridin-4-yl-oxy) aniline (90 mg, 0.31 mmol) and 4-chloro-3-trifluoromethylphenyl isocyanate (68.5 mg, 0.31 mmol) in dichloromethane (50 mL) was stirred at room temperature for 12 hours, and then filtrated, the resultant white solid was collected, washed with dichloromethane, and dried to get product as white solid (54 mg, yield: 34%).

$^1$H NMR (400 MHz, DMSO-d$_6$) δ 9.23 (s, 1H), 9.05 (s, 1H), 8.56 (d, J=6.0 Hz, 1H), 8.51 (s, 1H), 8.19 (s, 1H), 8.12 (d, J=2.0 Hz, 1H), 7.67-7.59 (m, 4H), 7.28 (d, J=9.0 Hz, 2H), 6.58 (d, J=6.0 Hz, 1H), 3.96 (s, 3H)

MS (ESI+): m/z 512.9 [M+H]$^+$

Example 5

FD-2013027

1-(4-chloro-3-(trifluoromethyl)phenyl)-3-(4-(3-methyl-2-(1-methyl-pyrazol-4-yl)-pyridin-4-yl-oxy)phenyl)urea

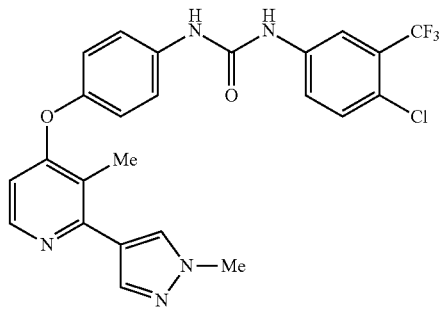 [SMILES: Cn1cc(-c2nccc(Oc3ccc(NC(=O)Nc4ccc(Cl)c(C(F)(F)F)c4)cc3)c2N)cn1]

Preparation Method

Step 1: Synthesis of 2-chloro-4-fluoro-3-methylpyridine

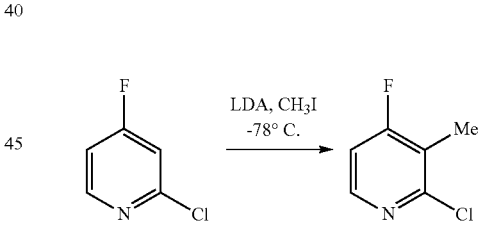

In an atmosphere of nitrogen gas, at −30° C., n-butyl lithium (2.4M hexane solution, 4.37 mL, 10.49 mmol) was added dropwise into a solution of diisopropylamine (1.06 g, 11 mmol) in anhydrous tetrahydrofuran (20 mL) to get a reaction mixture. The reaction mixture was stirred at −30° C. for 30 minutes, and then cooled to −78° C. A solution of 2-chloro-4-fluoropyridine (1.31 g, 10 mmol) in anhydrous tetrahydrofuran (10 mL) was added dropwise, and the reaction mixture was then stirred at −78° C. for 60 minutes. A solution of iodomethane (1.48 g, 10.5 mmol) in anhydrous tetrahydrofuran (5 mL) was added dropwise, and the reaction mixture was then stirred at −78° C. for 30 minutes. The reaction mixture was quenched with saturated ammonium chloride solution (5 mL), diluted with water (50 mL), and extracted with ethyl acetate (30 mL×3). The organic phases were combined. The combined organic phases were washed with saturated saline solution (30 mL×3), dried with anhydrous sodium sulfate, filtrated, and concentrated. The residue was purified by column chromatography (petroleum ether:ethyl acetate=100:1, v/v) to get product as yellow solid (0.63 g, yield: 43%).

$^1$H NMR (300 MHz, DMSO-d$_6$) δ 8.31 (dd, J=8.0, 5.8 Hz, 1H), 7.38 (dd, J=8.7, 5.6 Hz, 1H), 2.27 (d, J=1.8 Hz, 3H)

MS (ESI+): m/z 146.0 [M+H]$^+$

Step 2: Synthesis of 2-chloro-3-methyl-4-(4-aminophenoxy)pyridine

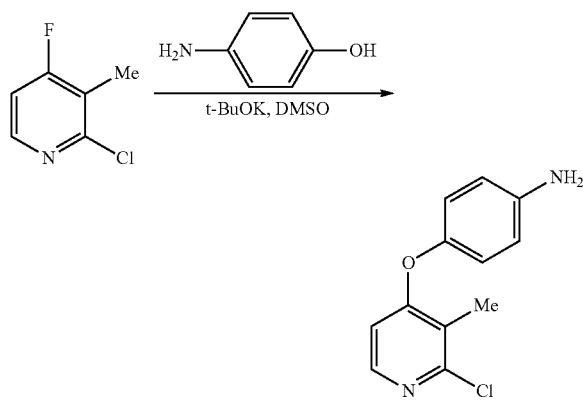

A solution of 4-aminophenol (0.21 g, 1.91 mmol) in anhydrous dimethyl sulfoxide (3 mL) was bubbled with nitrogen gas for 10 minutes, and potassium tert-butoxide (0.22 g, 1.96 mmol) was then added to get a reaction mixture. The reaction mixture was stirred at room temperature for 30 minutes, 2-chloro-4-fluoro-3-methylpyridine (269 mg, 1.85 mmol) was added. The reaction mixture was stirred at room temperature for 5 hours, and then diluted with water (20 mL) and extracted with ethyl acetate (20 mL×3). The organic phases were combined. The combined organic phases were washed with water (20 mL×2), washed with saline solution (20 mL×2), dried with anhydrous sodium sulfate, filtrated, and concentrated. The residue was purified by column chromatography (silica gel, petroleum ether:ethyl acetate=5:1, v/v) to get product as light yellow solid (0.38 g, yield: 88%).

$^1$H NMR (300 MHz, DMSO-d$_6$) δ 8.04 (d, J=5.6 Hz, 1H), 6.89-6.78 (m, 2H), 6.69-6.57 (m, 2H), 6.51 (d, J=5.7 Hz, 1H), 5.15 (s, 2H), 2.31 (s, 3H)

MS (ESI+): m/z 235.0 [M+H]$^+$

Step 3: Synthesis of 4-(3-methyl-2-(1-methyl-pyrazol-4-yl)-pyridin-4-yl-oxy)aniline

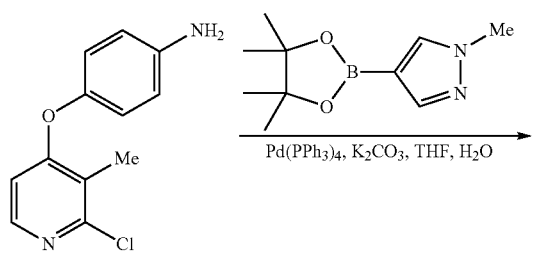

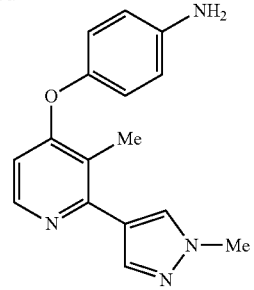

A mixture of 2-chloro-3-methyl-4-(4-aminophenoxy)pyridine (380 mg, 1.62 mmol), 1-methylpyrazol-4-yl-boronic acid pinacol ester (337 mg, 1.62 mmol), potassium carbonate (400 mg, 2.89 mmol) and tetrakis(triphenylphosphine)palladium (90 mg, 0.08 mmol) in tetrahydrofuran (THF, 6 mL) and water (1 mL) was bubbled with argon gas for 5 minutes, and then stirred in an atmosphere of argon gas at 85° C. for 24 hours to get a reaction mixture. The reaction mixture was diluted with water (20 mL), and extracted with ethyl acetate (20 mL×3). The organic phases were combined. The combined organic phases were washed with water (20 mL×2), washed with saturated saline solution (20 mL×2), dried with anhydrous sodium sulfate, filtrated, and concentrated. The residue was purified by column chromatography (silica gel, petroleum ether:ethyl acetate=1:2, v/v) to get product as light yellow solid (170 mg, yield: 37.5%).

$^1$H NMR (400 MHz, DMSO-d$_6$) δ 8.18 (d, J=5.6 Hz, 1H), 8.17 (s, 1H), 7.88 (s, 1H), 6.82 (d, J=8.7 Hz, 2H), 6.63 (d, J=8.7 Hz, 2H), 6.35 (d, J=5.6 Hz, 1H), 5.10 (s, 2H), 3.91 (s, 3H), 2.39 (s, 3H)

MS (ESI+): m/z 281.1 [M+H]$^+$

Step 4: Synthesis of 1-(4-chloro-3-(trifluoromethyl)phenyl)-3-(4-(3-methyl-2-(1-methyl-pyrazol-4-yl)-pyridin-4-yl-oxy)phenyl)urea

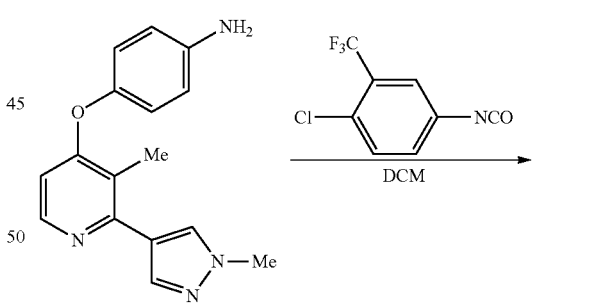

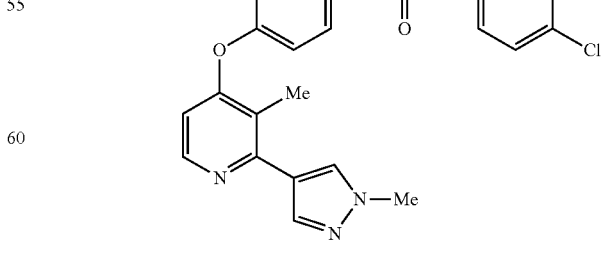

A solution of 4-(3-methyl-2-(1-methyl-pyrazol-4-yl)-pyridin-4-yl-oxy)aniline (165 mg, 0.58 mmol) and 4-chloro- 3-trifluoromethylphenyl isocyanate (155 mg, 0.7 mmol) in dichloromethane (2 mL) was stirred at room temperature for 12 hours, and then filtrated, then the resultant white solid was collected, washed with dichloromethane, and dried to get product as white solid (145 mg, yield: 49%).

$^1$H NMR (300 MHz, DMSO-d$_6$) δ 9.18 (s, 1H), 8.94 (s, 1H), 8.24 (d, J=5.4 Hz, 1H), 8.19 (s, 1H), 8.12 (d, J=2.1 Hz, 1H), 7.91 (s, 1H), 7.69-7.58 (m, 2H), 7.55 (d, J=9.0 Hz, 2H), 7.09 (d, J=9.0 Hz, 2H), 6.47 (d, J=5.4 Hz, 1H), 3.92 (s, 3H), 2.40 (s, 3H)

MS (ESI+): m/z 501.9 [M+H]$^+$

Example 6

FD-2013031

1-(4-chloro-3-(trifluoromethyl)phenyl)-3-(4-(3-amino-2-(1-methyl-pyrazol-4-yl)-pyridin-4-yl-oxy)phenyl)urea

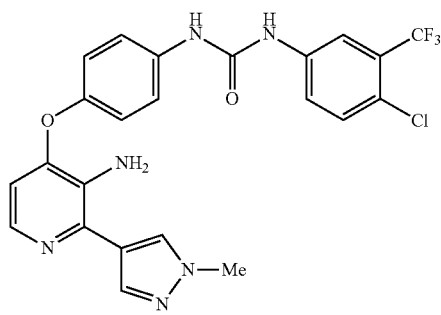

Preparation Method

Step 1: Synthesis of
2-chloro-3-nitro-4-(4-aminophenoxy)pyridine

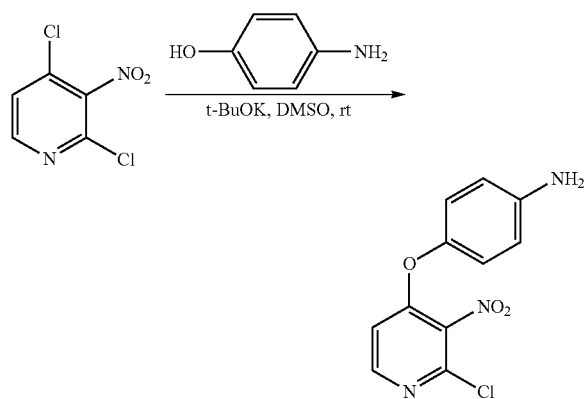

A solution of 4-aminophenol (1.09 g, 10 mmol) in anhydrous dimethyl sulfoxide (10 mL) was bubbled with nitrogen gas for 10 minutes, and potassium tert-butoxide (1.12 g, 10 mmol) was then added to get a reaction mixture. The reaction mixture was stirred at room temperature for 15 minutes, 2,4-dichloro-3-nitropyridine (1.93 g, 10 mmol) was added. The reaction mixture was stirred at room temperature for 5 hours, and then diluted with water (100 mL), and extracted with ethyl acetate (50 mL×3). The organic phases were combined. The combined organic phases were washed with water (50 mL×2), washed with saline solution (50 mL×2), dried with anhydrous sodium sulfate, filtrated, and concentrated. The residue was purified by column chromatography (silica gel, petroleum ether:ethyl acetate=3:1, v/v) to get product as light yellow solid (408 mg, yield: 15%).

$^1$H NMR (300 MHz, DMSO-d$_6$) δ 8.40 (d, J=5.7 Hz, 1H), 6.33 (d, J=8.7 Hz, 2H), 6.28 (d, J=5.7 Hz, 2H), 6.63 (d, J=8.7 Hz, 2H), 5.30 (br s, 2H)

MS (ESI+): m/z 266.0 [M+H]$^+$

Step 2: Synthesis of 4-(3-nitro-2-(1-methyl-pyrazol-4-yl)-pyridin-4-yl-oxy)aniline

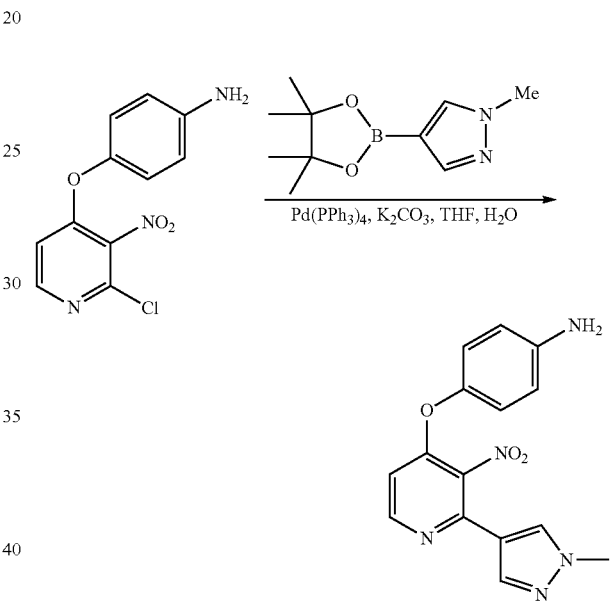

A mixture of 2-chloro-3-nitro-4-(4-aminophenoxy)pyridine (1.25 mg, 1.51 mmol), 1-methylpyrazol-4-yl-boronic acid pinacol ester (377 mg, 1.81 mmol), potassium carbonate (12.4 g, 9.0 mmol) and tetrakis(triphenylphosphine) palladium (174 mg, 1.151 mmol) in tetrahydrofuran (THF, 18 mL) and water (3 mL) was bubbled with argon gas for 5 minutes, and stirred in an atmosphere of argon gas at 85° C. overnight to get a reaction mixture. The reaction mixture was diluted with water (50 mL), and extracted with ethyl acetate (30 mL×3). The organic phases were combined. The combined organic phases were washed with water (30 mL×2), washed with saturated saline solution (30 mL×2), dried with anhydrous sodium sulfate, filtrated, and concentrated. The residue was purified by column chromatography (silica gel, petroleum ether:ethyl acetate=1:3, v/v) to get product as light yellow solid (450 mg, yield: 96%).

$^1$H NMR (300 MHz, DMSO-d$_6$) δ 8.49 (d, J=5.7 Hz, 1H), 8.10 (s, 1H), 7.72 (s, 1H), 7.69-7.46 (m, 11H), 6.91 (d, J=8.7 Hz, 2H), 6.68 (d, J=5.7 Hz, 1H), 6.63 (d, J=8.7 Hz, 2H), 5.26 (br s, 2H), 3.91 (s, 3H)

MS (ESI+) m/z 312.0 [M+H]$^+$

Step 3: Synthesis of 4-(3-amino-2-(1-methyl-pyrazol-4-yl)-pyridin-4-yl-oxy)aniline

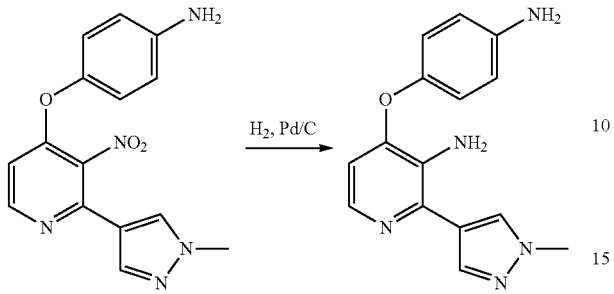

A mixture of 4-(3-nitro-2-(1-methyl-pyrazol-4-yl)-pyridin-4-yl-oxy) aniline (200 mg, 0.64 mmol) and Palladium-Carbon (20 mg) in anhydrous methanol (15 mL) was stirred at room temperature in an atmosphere of 4 atm hydrogen gas for 4 hours. Palladium-Carbon was filtrated through Celite, and then the filtrate was concentrated. The residue was purified by column chromatography (silica gel, petroleum ether:ethyl acetate=1:4) to get product (75 mg, yield: 41%).

$^1$H NMR (400 MHz, DMSO-$d_6$) δ 8.20 (s, 1H), 7.91 (s, 1H), 7.73 (d, J=5.2 Hz, 1H), 6.83 (d, J=8.8 Hz, 2H), 6.62 (d, J=8.8 Hz, 2H), 6.29 (d, J=5.2 Hz, 1H), 5.08 (br s, 2H), 4.72 (s, 2H), 3.90 (s, 3H)

MS (ESI+): m/z 282.1 [M+H]$^+$

Step 4: Synthesis of 1-(4-chloro-3-(trifluoromethyl)phenyl)-3-(4-(3-amino-2-(1-methyl-pyrazol-4-yl)-pyridin-4-yl-oxy)phenyl)urea

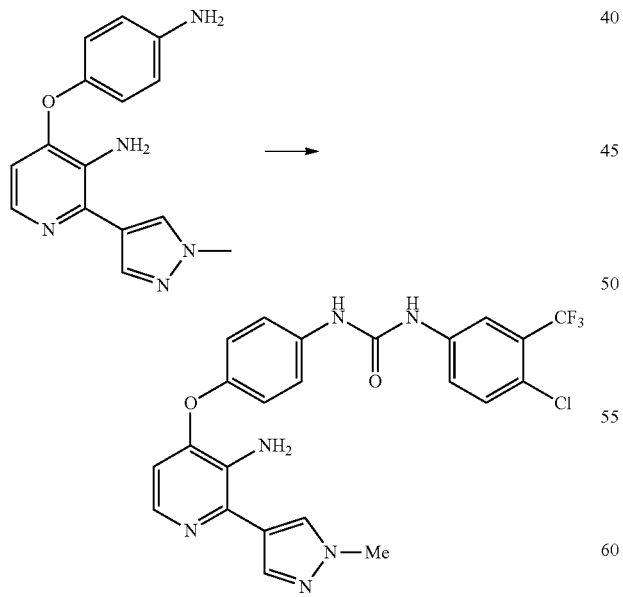

A solution of 4-(3-amino-2-(1-methyl-pyrazol-4-yl)-pyridin-4-yl-oxy)aniline (70 mg, 0.249 mmol) and 4-chloro-3-trifluoromethylphenyl isocyanate (55 mg, 0.249 mmol) in dichloromethane (3 mL) was stirred at room temperature for 3 hours, and then filtrated, the resultant white solid was collected, washed with dichloromethane, and dried to get product as white solid (79 mg, yield: 63%).

$^1$H NMR (300 MHz, DMSO-$d_6$) δ 9.17 (s, 1H), 8.92 (s, 1H), 8.23 (s, 1H), 8.11 (s, 1H), 7.93 (s, 1H), 7.78 (d, J=5.4 Hz, 1H), 7.63 (d, J=2.6 Hz, 2H), 7.67-7.59 (m, 2H), 7.10 (d, J=9.0 Hz, 2H), 6.42 (d, J=5.4 Hz, 1H), 4.82 (br s, 2H), 3.91 (s, 3H)

MS (ESI+): m/z 502.9 [M+H]$^+$

Example 7

FD-2013033

1-(4-chloro-3-(trifluoromethyl)phenyl)-3-(4-(3-methylamino-2-(1-methyl-pyrazol-4-yl)-pyridin-4-yl-oxy)phenyl)urea

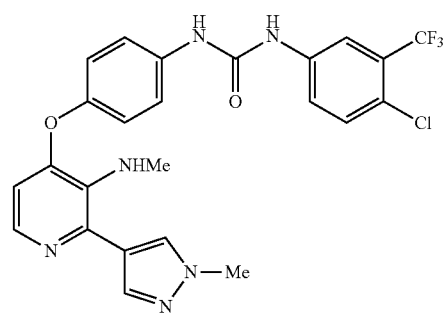 [SMILES: CNc1c(Oc2ccc(NC(=O)Nc3ccc(Cl)c(C(F)(F)F)c3)cc2)ccnc1-c1cnn(C)c1]

Preparation Method

Step 1: Synthesis of 2-chloro-4-iodo-3-(methylamino)pyridine

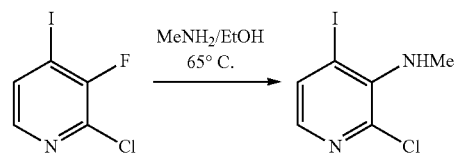 [SMILES: Fc1c(I)ccnc1Cl ; CNc1c(I)ccnc1Cl]

In a sealed tube, a solution of 2-chloro-3-fluoro-4-iodopyridine (12 g, 46.6 mmol) in aminomethane and ethanol (25%, v/v, 30 mL) was stirred at 65° C. for 8 hours. The volatile substance was removed under reduced pressure. The residue was purified by column chromatography (silica gel, petroleum ether:ethyl acetate=30:1) to get product as yellow oil (5.5 g, yield: 44%).

$^1$H NMR (300 MHz, DMSO-$d_6$) δ 7.77 (d, J=4.9 Hz, 1H), 7.51 (d, J=4.9 Hz, 1H), 4.75 (br, s, 1H), 2.91 (s, 3H)

MS (ESI+): m/z 268.9 [M+H]$^+$

Step 2: Synthesis of 2-chloro-3-methylamino-4-(4-aminophenoxy) pyridine

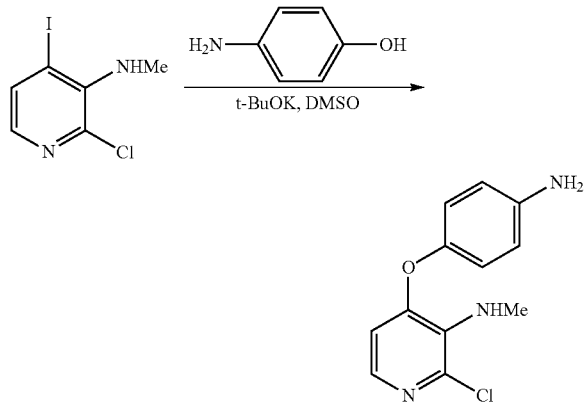

A solution of 4-aminophenol (0.16 g, 1.46 mmol)) in anhydrous dimethyl sulfoxide (3 mL) was bubbled with nitrogen gas for 10 minutes, and potassium tert-butoxide (0.16 g, 1.46 mmol) was then added to get a reaction mixture. The reaction mixture was stirred at room temperature for 30 minutes, then 2-chloro-4-iodo-3-(methylamino) pyridine (170 mg, 0.63 mmol) was added. The reaction mixture was stirred at room temperature for 1 hours, and then stirred at 80° C. for 5 hours. The reaction mixture was diluted with water (20 mL) and extracted with ethyl acetate (20 mL×3). The organic phases were combined. The combined organic phases were washed with water (20 mL×2), washed with saline solution (20 mL×2), dried with anhydrous sodium sulfate, filtrated, and concentrated. The residue was purified by column chromatography (silica gel, petroleum ether:ethyl acetate=5:1, v/v) to get product as light yellow solid (96 mg, yield: 61%).

$^1$H NMR (400 MHz, DMSO-$d_6$) δ 7.57 (d, J=5.3 Hz, 1H), 6.81 (d, J=8.8 Hz, 2H), 6.66-6.56 (m, 2H), 6.48 (d, J=5.3 Hz, 1H), 5.08 (s, 2H), 4.94 (q, J=5.4 Hz, 1H), 2.97 (d, J=5.4 Hz, 3H)

MS (ESI+): m/z 250.0 [M+H]$^+$

Step 3: Synthesis of 4-(3-methylamino-2-(1-methyl-pyrazol-4-yl)-pyridin-4-yl-oxy)aniline

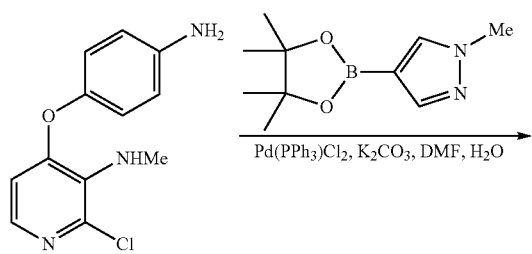

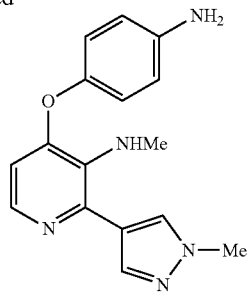

A mixture of 2-chloro-3-methylamino-4-(4-aminophenoxy)pyridine (270 mg, 1.08 mmol), 1-methylpyrazol-4-yl-boronic acid pinacol ester (225 mg, 1.08 mmol), potassium carbonate (447 mg, 3.24 mmol) and Bis(triphenylphosphine)dichloropalladium (II) (76 mg, 0.108 mmol) in dimethylformamide (DMF, 6 mL) and water (1 mL) was bubbled with argon gas for 5 minutes, and then stirred in an atmosphere of argon gas at 85° C. for 24 hours to get a reaction mixture. The reaction mixture was diluted with water (30 mL), and extracted with ethyl acetate (30 mL×3). The organic phases were combined. The combined organic phases were washed with water (30 mL×2), washed with saturated saline solution (30 mL×2), dried with anhydrous sodium sulfate, filtrated, and concentrated. The residue was purified by column chromatography (silica gel, petroleum ether:ethyl acetate=1:3, v/v) to get product as light yellow solid (180 mg, yield: 56%).

$^1$H NMR (400 MHz, DMSO-$d_6$) δ 8.19 (s, 1H), 8.02 (s, 1H), 7.94 (s, 1H), 7.91 (d, J=5.4 Hz, 1H), 6.84 (d, J=8.7 Hz, 2H), 6.62 (d, J=8.7 Hz, 2H), 6.35 (d, J=5.4 Hz, 1H), 5.14 (s, 1H), 3.90 (s, 3H), 2.66 (s, 3H)

MS (ESI+): m/z 296.1 [M+H]$^+$

Step 4: Synthesis of 1-(4-chloro-3-(trifluoromethyl) phenyl)-3-(4-(3-methyl amino-2-(1-methyl-pyrazol-4-yl)-pyridin-4-yl-oxy)phenyl)urea

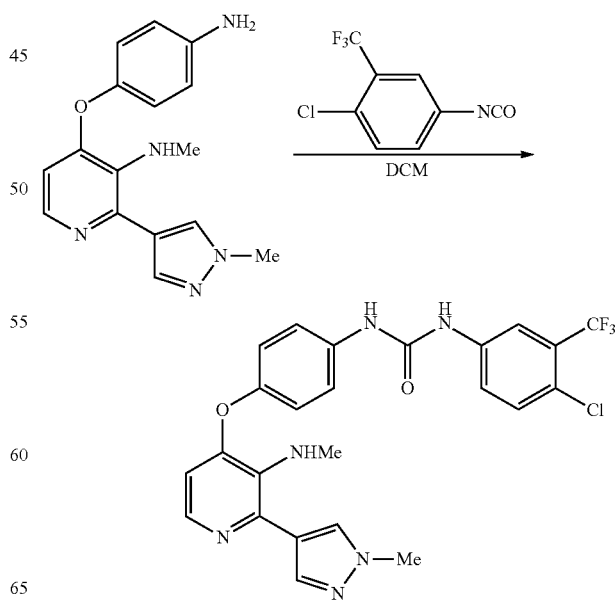

A solution of 4-(3-methylamino-2-(1-methyl-pyrazol-4-yl)-pyridin-4-yl-oxy)aniline (170 mg, 0.576 mmol) and 4-chloro-3-trifluoromethyl phenyl isocyanate (127.6 mg, 0.576 mmol) in dichloromethane (2 mL) was stirred at room temperature for 12 hours, and then filtrated, the resultant white solid was collected, washed with dichloromethane, and dried to get product as white solid (67 mg, yield: 22.5%).

$^1$H NMR (300 MHz, DMSO-$d_6$) δ 9.16 (s, 1H), 8.91 (s, 1H), 8.20 (s, 1H), 8.11 (s, 1H), 7.95 (d, J=5.1 Hz, 2H), 7.94 (s, 1H), 7.66-7.60 (m, 2H), 7.53 (d, J=9.0 Hz, 2H), 7.09 (d, J=9.0 Hz, 2H), 6.47 (d, J=5.1 Hz, 1H), 4.40 (br s, 1H), 3.91 (s, 3H), 2.69 (d, J=4.8 Hz, 3H)

MS (ESI+): m/z 517.1[M+H]$^+$

Example 8

FD-2013037

1-(4-chloro-3-(trifluoromethyl)phenyl)-3-(4-(3-methoxy-2-(1-methyl-pyrazol-4-yl)-pyridin-4-yl-oxy)phenyl)urea

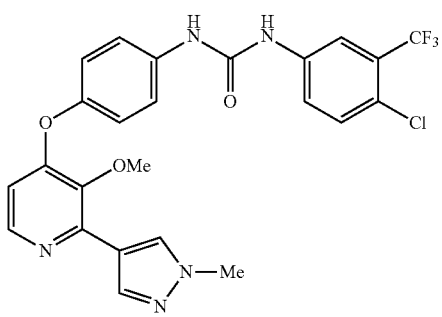 [SMILES: COc1c(Oc2ccc(NC(=O)Nc3ccc(Cl)c(C(F)(F)F)c3)cc2)ccnc1-c1cnn(C)c1]

Preparation Method

Step 1: Synthesis of 2-chloro-3-methoxy-4-iodopyridine

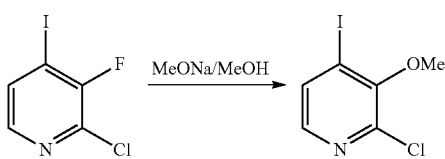 [SMILES: Fc1c(I)ccnc1Cl ; COc1c(I)ccnc1Cl]

A solution of 2-chloro-3-fluoro-4-iodopyridine (1.05 g, 4.08 mmol) and sodium methoxide (0.22 g, 4.08 mmol) in methanol (10 mL) was stirred at 45° C. for 2 hours to get a reaction mixture. The reaction mixture was diluted with water (50 mL), and extracted with ethyl acetate (50 mL×3). The organic phases were combined. The combined organic phases were washed with water (50 mL×2), washed with saline solution (50 mL×2), dried with anhydrous sodium sulfate, filtrated, and concentrated. The residue was purified by column chromatography (silica gel, petroleum ether:ethyl acetate=100:1, v/v) to get product as light yellow solid (0.58 g product, yield: 53%).

$^1$H NMR (300 MHz, DMSO-$d_6$) δ 7.92 (d, J=5.1 Hz, 1H), 7.86 (d, J=5.1 Hz, 1H), 3.83 (s, 3H)

MS (ESI+): m/z 269.8 [M+H]$^+$

Step 2: Synthesis of 2-chloro-3-methoxy-4-(4-aminophenoxy) pyridine

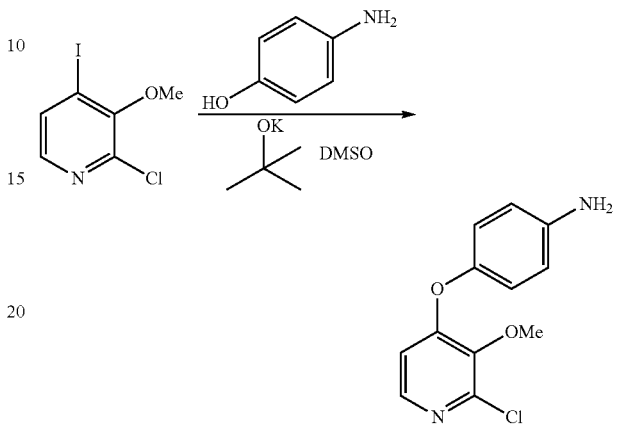

In a sealed tube, a solution of 4-aminophenol (0.172 g, 1.58 mmol), 2-chloro-3-methoxy-4-iodopyridine (425 mg, 1.58 mmol) and potassium tert-butoxide (0.177 g, 1.58 mmol) in anhydrous dimethyl sulfoxide (5 mL) was stirred at 155° C. for 2.5 hours to get a reaction mixture. The reaction mixture was diluted with water (30 mL), and extracted with ethyl acetate (30 mL×3). The organic phases were combined. The combined organic phases were washed with water (30 mL×2), washed with saline solution (30 mL×2), dried with anhydrous sodium sulfate, filtrated, and concentrated. The residue was purified by column chromatography (silica gel, petroleum ether:ethyl acetate=4:1, v/v) to get product as light yellow solid (210 mg, yield: 53%).

$^1$H NMR (300 MHz, DMSO-$d_6$) δ 7.95 (d, J=5.7 Hz, 1H), 6.91-6.86 (d, J=8.7 Hz, 2H), 6.63 (d, J=8.7 Hz, 2H), 6.62 (d, J=5.7 Hz, 1H), 5.16 (s, 2H), 3.90 (s, 3H)

MS (ESI+): m/z 251.0 [M+H]$^+$

Step 3: Synthesis of 4-(3-methoxy-2-(1-methyl-pyrazol-4-yl)-pyridin-4-yl-oxy)aniline

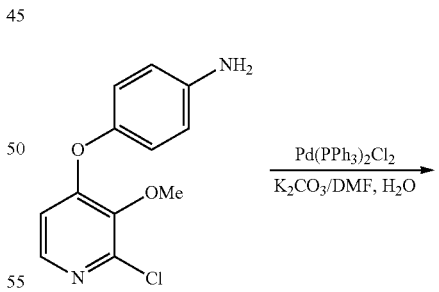

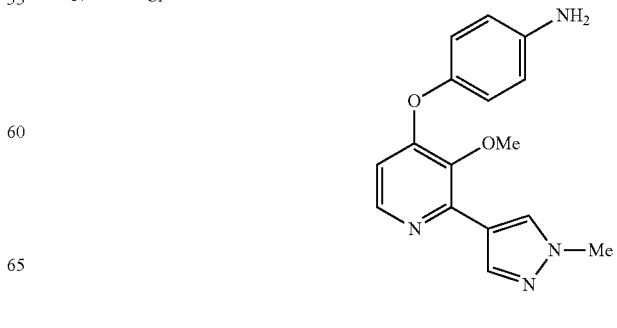

A mixture of 2-chloro-3-methoxy-4-(4-aminophenoxy) pyridine (130 mg, 0.52 mmol), 1-methylpyrazol-4-yl-boronic acid pinacol ester (120 mg, 0.58 mmol), potassium carbonate (215 mg, 1.56 mmol) and bis(triphenylphosphine) dichloropalladium (II) (90 mg, 0.127 mmol) in dimethylformamide (DMF, 6 mL) and water (1 mL) was bubbled with argon gas for 5 minutes, and then stirred in an atmosphere of argon gas at 100° C. for 5 hours to get a reaction mixture. The reaction mixture was diluted with water (30 mL), and extracted with ethyl acetate (30 mL×3). The organic phases were combined. The combined organic phases were washed with water (30 mL×2), washed with saturated saline solution (30 mL×2), dried with anhydrous sodium sulfate, filtrated, and concentrated. The residue was purified by column chromatography (silica gel, petroleum ether:ethyl acetate=1:3, v/v) to get product as light yellow solid (40 mg, yield: 26%).

$^1$H NMR (300 MHz, DMSO-d$_6$) δ 8.27 (s, 1H), 8.07 (d, J=5.4 Hz, 1H), 8.00 (s, 1H), 6.87 (d, J=8.7 Hz, 2H), 6.62 (d, J=8.7 Hz, 2H), 6.41 (d, J=5.4 Hz, 1H), 5.12 (s, 2H), 3.91 (s, 3H), 3.89 (s, 3H)

MS (ESI+): m/z 297.1 [M+H]$^+$

Step 4: Synthesis of 1-(4-chloro-3-(trifluoromethyl)phenyl)-3-(4-(3-methoxy-2-(1-methyl-pyrazol-4-yl)-pyridin-4-yl-oxy)phenyl)urea

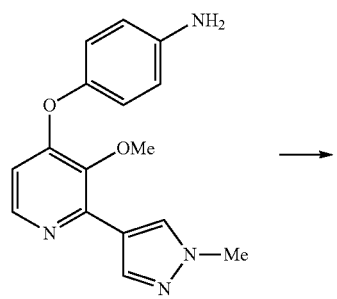

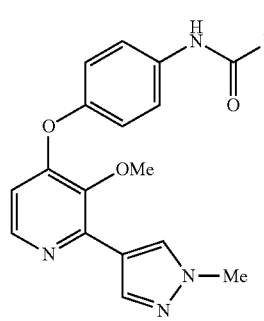

A solution of 4-(3-methoxy-2-(1-methyl-pyrazol-4-yl)-pyridin-4-yl-oxy)aniline (40 mg, 0.135 mmol) and 4-chloro-3-trifluoromethylphenyl isocyanate (30 mg, 0.135 mmol) in dichloromethane (5 mL) was stirred at room temperature for 12 hours, and then filtrated, then the resultant white solid was collected, washed with dichloromethane, and dried to get product as white solid (50 mg, yield: 71%).

$^1$H NMR (300 MHz, DMSO-d$_6$) δ 9.18 (s, 1H), 8.95 (s, 1H), 8.30 (s, 1H), 8.17-8.08 (m, 2H), 8.02 (s, 1H), 7.69-7.59 (m, 2H), 7.55 (d, J=9.0 Hz, 2H), 7.15 (d, J=9.0 Hz, 2H), 6.55 (d, J=5.4 Hz, 1H), 3.91 (s, 3H), 3.89 (s, 3H)

MS (ESI+): m/z 517.9 [M+H]$^+$

Comparative Example 1

Comparative Compound: Sorafenib free base, prepared by the method as disclosed in the patent application document WO0042012A1.

Comparative Example 2

Compound No. FD-1210005

Compound of Example 1 disclosed in CN201110435847.9

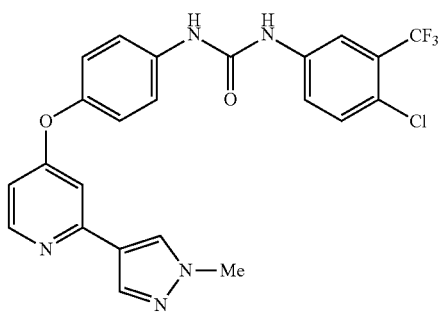 [SMILES: Cn1cc(-c2cc(Oc3ccc(NC(=O)Nc4ccc(Cl)c(C(F)(F)F)c4)cc3)ccn2)cn1]

Preparation Method

Step 1: Synthesis of 2-chloro-4-(4-aminophenoxy)pyridine

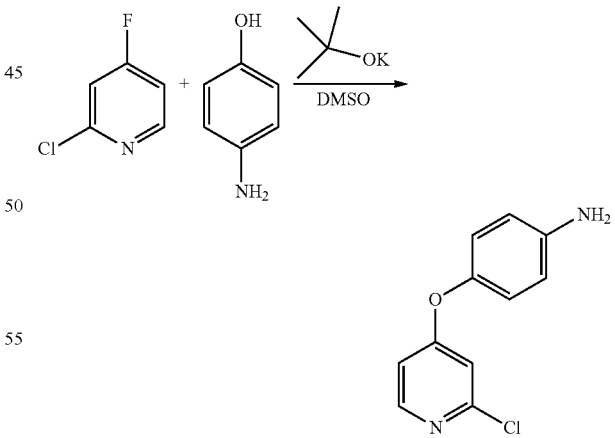

A solution of 4-aminophenol (4.35 g, 39.8 mmol) in 40 mL anhydrous dimethyl sulfoxide was bubbled with nitrogen gas for 10 minutes, and potassium tert-butoxide (4.7 g, 41.8 mmol) was then added, stirred at room temperature for 30 minutes, and then 2-chloro-4-fluoropyridine (5 g, 38.0 mmol) was added to get a reaction mixture. The reaction mixture was slowly heated to 80° C. and reacted at the temperature for 2 hours, cooled to room temperature when TLC showed that the reaction was finished, then diluted with water (100 mL), and extracted with ethyl acetate (100 mL×3). The ethyl acetate phases were combined, washed with water (100 mL×2), washed with saline solution again (100 mL), dried with anhydrous sodium sulfate, filtrated and concentrated. The residue was purified by column chromatography (silica gel, petroleum ether:ethyl acetate=4:1, v/v) to get product as light yellow solid (7.26 g, yield: 86.8%). $^1$H NMR (300 MHz, CDCl$_3$): δ 4.07 (br s, 2H), 6.72 (d, J=8.7 Hz, 2H), 6.75-6.77 (m, 2H), 6.88 (d, J=8.7 Hz, 2H), 8.19 (d, J=5.4 Hz, 1H).

MS (ESI+): 221.1 [M+H]$^+$

Step 2: Synthesis of 4-(2-(1-methyl-pyrazol-4-yl)-pyridin-4-yl-oxy) aniline

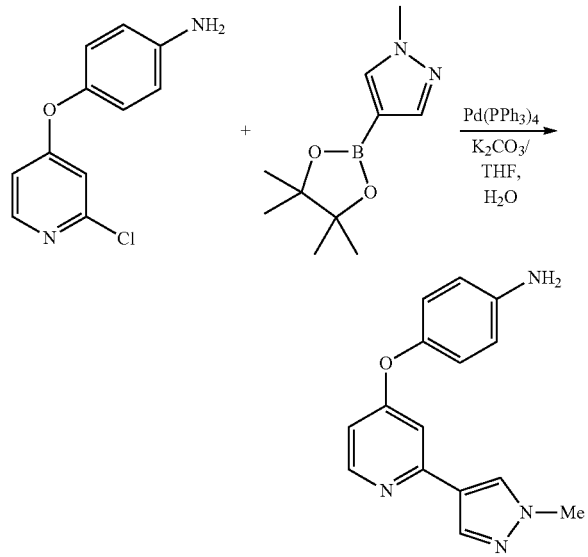

Under the protection of nitrogen gas, 2-chloro-4-(4-aminophenoxy)pyridine (5.7 g, 25.9 mmol) and 1-methyl-pyrazol-4-yl-boronic acid pinacol ester (6.47 g, 31.1 mmol) were dissolved in tetrahydrofuran (THF, 70 mL). Under stirring, potassium carbonate (10.7 g, 77.5 mmol) and water (17.1 mL) were added, and tetrakis(triphenylphosphine) palladium as a catalyst (1.5 g, 1.29 mmol) was then added in dark, stirred at 70° C. for 24 hours, cooled to room temperature, concentrated, and then diluted with water (50 mL), and extracted with ethyl acetate (50 mL×3). The ethyl acetate phases were combined, washed with water (50 mL×2), washed with saline solution again (50 mL), dried with anhydrous sodium sulfate, filtrated, and concentrated. The residue was purified by column chromatography (silica gel, petroleum ether:ethyl acetate=1:2, v/v) to get product as light yellow solid (5.85 g, yield: 85%).

$^1$H NMR (300 MHz, CDCl$_3$): δ 3.84 (br s, 2H), 3.92 (s, 3H), 6.60 (dd, J=2.4, 5.7 Hz, 1H), 6.71 (d, J=8.7 Hz, 2H), 6.91 (d, J=8.7 Hz, 2H), 6.94 (d, J=2.1 Hz, 1H), 7.86 (s, 2H,), 8.34 (d, J=5.7 Hz, 1H). MS (ESI+): 267.1 [M+H]$^+$

Step 3: Synthesis of 1-(4-chloro-3-(trifluoromethyl)phenyl)-3-(4-(2-(1-methyl-pyrazol-4-yl)-pyridin-4-yl-oxy)phenyl)urea

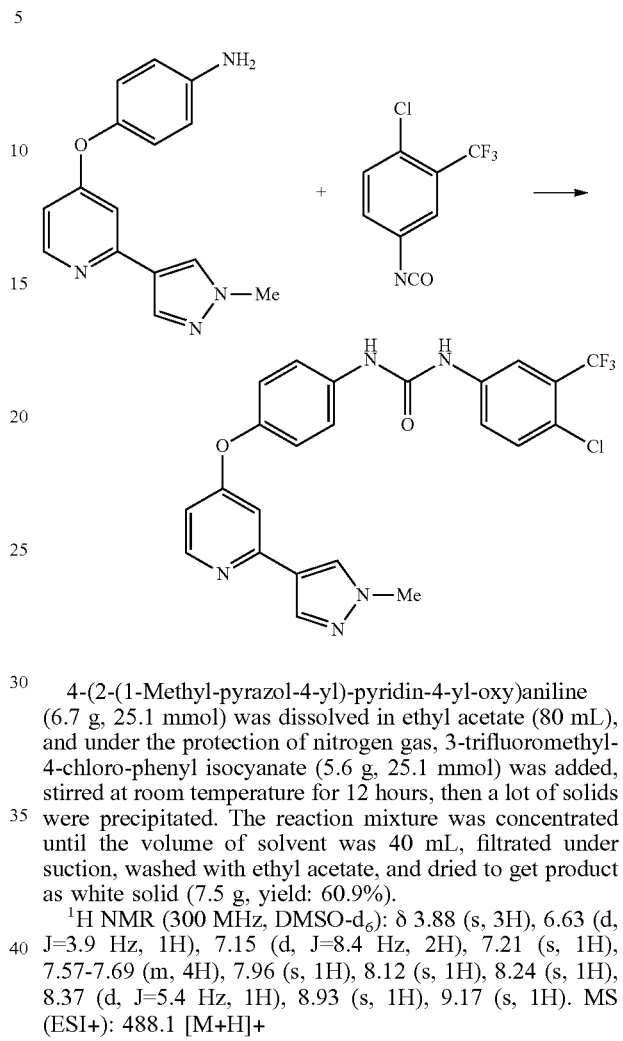

4-(2-(1-Methyl-pyrazol-4-yl)-pyridin-4-yl-oxy)aniline (6.7 g, 25.1 mmol) was dissolved in ethyl acetate (80 mL), and under the protection of nitrogen gas, 3-trifluoromethyl-4-chloro-phenyl isocyanate (5.6 g, 25.1 mmol) was added, stirred at room temperature for 12 hours, then a lot of solids were precipitated. The reaction mixture was concentrated until the volume of solvent was 40 mL, filtrated under suction, washed with ethyl acetate, and dried to get product as white solid (7.5 g, yield: 60.9%).

$^1$H NMR (300 MHz, DMSO-d$_6$): δ 3.88 (s, 3H), 6.63 (d, J=3.9 Hz, 1H), 7.15 (d, J=8.4 Hz, 2H), 7.21 (s, 1H), 7.57-7.69 (m, 4H), 7.96 (s, 1H), 8.12 (s, 1H), 8.24 (s, 1H), 8.37 (d, J=5.4 Hz, 1H), 8.93 (s, 1H), 9.17 (s, 1H). MS (ESI+): 488.1 [M+H]+

Comparative Example 3

Compound No. FD-2013016

1-(4-chloro-3-(trifluoromethyl)phenyl)-3-(4-(2-(1-methyl-pyrazol-4-yl)-5-fluoro-pyridin-4-yl-oxy)phenyl)urea

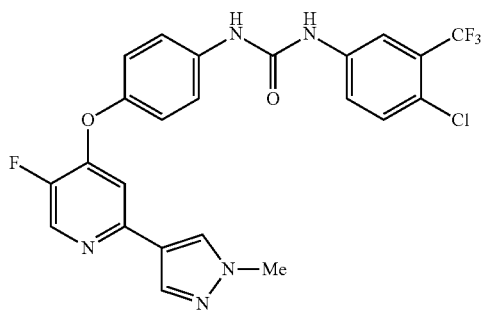 [SMILES: Cn1cc(-c2cc(Oc3ccc(NC(=O)Nc4ccc(Cl)c(C(F)(F)F)c4)cc3)c(F)cn2)cn1]

Preparation Method

Step 1: Synthesis of 2-chloro-4-iodo-5-fluoropyridine

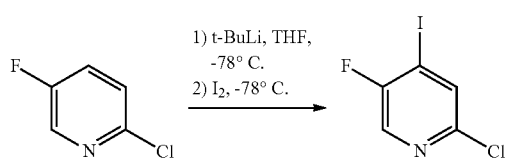 [SMILES: Fc1ccc(Cl)nc1 ; Fc1cnc(Cl)cc1I]

In a 100 mL three necked flask, 2-chloro-5-fluoropyridine (2.65 g, 20.1 mmol) was dissolved in anhydrous tetrahydrofuran (30 mL), and under a protection of nitrogen gas, stirred at −78° C. for 30 minutes. A solution of tert-butyl lithium (1.3M) in n-pentane (16.27 mL, 21.1 mmol) was slowly added dropwise, after the addition, the reaction was reacted at the temperature for 90 minutes. A solution of iodine (6.13 g, 24.2 mmol) in anhydrous tetrahydrofuran (10 mL) was then slowly added dropwise. After the addition, the temperature was slowly increased to room temperature. Saturated ammonium chloride solution (100 mL) was added, and water (50 mL) was then added, and then phase separation was performed, water phase was separately extracted with 50 mL, 40 mL, 200 mL ethyl acetate once. The organic phases were combined, and the organic phases were washed with saturated sodium thiosulfate solution (50 mL×2), washed with saline solution (50 mL×2), dried with anhydrous sodium sulfate, filtrated, and concentrated. The residue was purified by column chromatography (silica gel, petroleum ether:ethyl acetate=100:1, v/v) to get product as yellow solid (2 g, yield: 39%).

MS (ESI+): 257.9 [M+H]+

Step 2: Synthesis of 2-chloro-5-fluoro-4-(4-aminophenoxy)pyridine

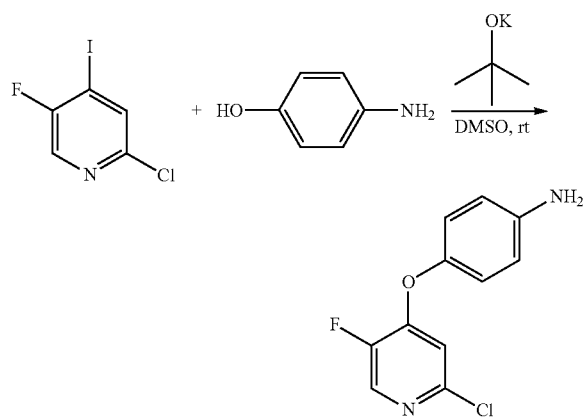

4-Aminophenol (0.55 g, 5 mmol) was dissolved in anhydrous dimethyl sulfoxide (15 mL), purged with nitrogen gas for 10 minutes, then potassium tert-butoxide (0.58 g, 5.2 mmol) was added, stirred at room temperature for 30 minutes, 2-chloro-4-iodo-5-fluoropyridine (1.3 g, 5 mmol) was added, reacted at room temperature for 5 hours. TLC showed that the reaction was finished. Ethyl acetate (50 mL) was added, sufficiently stirred, then water (100 mL) was added, and then phase separation was performed, water phase was extracted with ethyl acetate (50 mL×3). The ethyl acetate phases were combined, washed with water (50 mL×2), washed with saline solution again (50 mL×2), dried with anhydrous sodium sulfate, filtrated, and concentrated. The residue was purified by column chromatography (silica gel, petroleum ether:ethyl acetate=4:1, v/v) to get product as light yellow solid (0.2 g, yield: 16.8%).

$^1$H NMR (300 MHz, DMSO-$d_6$): δ 5.24 (br s, 2H), 6.64 (d, J=8.7 Hz, 2H), 6.65 (s, 1H), 6.94 (d, J=8.7 Hz, 2H), 8.44 (d, J=3.0 Hz, 1H). MS (ESI+): 239.1 [M+H]+

Step 3: Synthesis of 4-(5-fluoro-2-(1-methyl-pyrazol-4-yl)-pyridin-4-yl-oxy)aniline

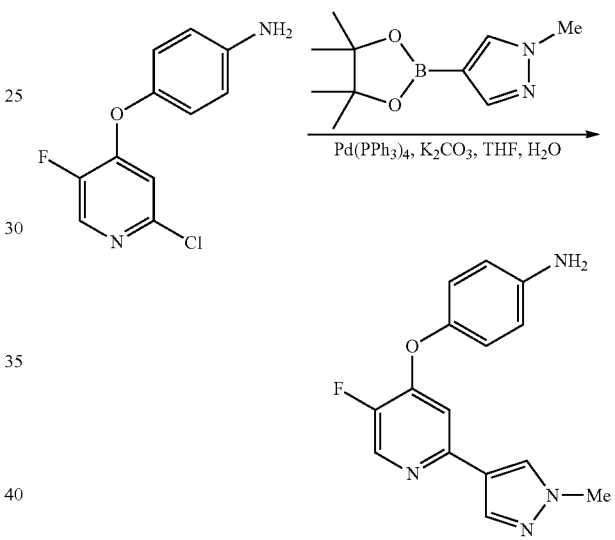

Under the protection of nitrogen gas, 2-chloro-5-fluoro-4-(4-amino phenoxy)pyridine (200 mg, 0.84 mmol) and 1-methylpyrazol-4-boronic acid pinacol ester (175 mg, 0.84 mmol) were dissolved in tetrahydrofuran (THF, 5 mL), potassium carbonate (347 mg, 2.51 mmol) and water (0.84 mL) were added, oxygen was removed, and under the protection of argon gas, tetrakis(triphenylphosphine)palladium as a catalyst (48 mg, 0.04 mmol) was added in dark, stirred at 85° C. for 24 hours, then cooled to room temperature when TLC showed that the reaction was finished. Ethyl acetate and water were then added (20 mL for each), phase separation was performed, water phase was extracted with ethyl acetate (20 mL×2). The ethyl acetate phases were combined, washed with saline solution (20 mL×2), dried with anhydrous sodium sulfate, filtrated, and concentrated. The residue was purified by column chromatography (silica gel, petroleum ether:ethyl acetate=4:1, v/v) to get product as light yellow solid (50 mg, yield: 21%).

$^1$H NMR (300 MHz, DMSO-$d_6$): δ 3.82 (s, 3H), 5.16 (br s, 2H), 6.63 (d, J=8.7 Hz, 2H), 6.89 (d, J=6.6 Hz, 1H), 6.91 (d, J=8.7 Hz, 2H), 7.76 (s, 1H), 8.10 (s, 1H), 8.46 (d, J=3.0 Hz, 1H). MS (ESI+): 285.0 [M+H]+

Step 4: Synthesis of 1-(4-chloro-3-(trifluoromethyl)phenyl)-3-(4-(5-fluoro-2-(1-methyl-pyrazol-4-yl)-pyridin-4-yl-oxy)phenyl)urea

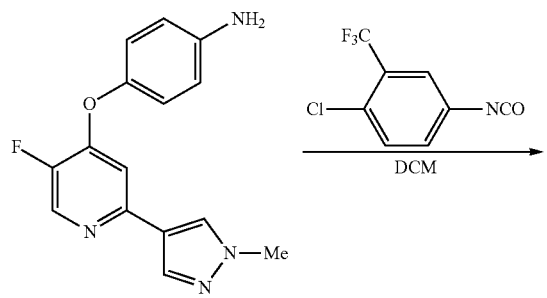

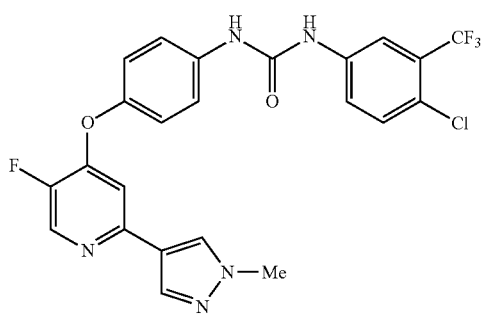

4-(5-fluoro-2-(1-methyl-pyrazol-4-yl)-pyridin-4-yl-oxy)aniline (50 mg, 0.176 mmol) was dissolved in dichloromethane (2 mL), and under a protection of nitrogen gas, 4-chloro-3-trifluoromethylphenyl isocyanate (46 mg, 0.208 mmol) was added stirred at room temperature for 12 hours. A lot of solids were precipitated, filtrated under suction, washed with dichloromethane, and dried to get product as white solid (61 mg, yield: 68.6%).

$^1$H NMR (300 MHz, DMSO-d$_6$): δ 3.83 (s, 3H), 7.11 (d, J=6.6 Hz, 1H), 7.18 (d, J=9.0 Hz, 2H), 7.56 (d, J=9.0 Hz, 2H), 7.60-7.67 (m, 2H), 7.83 (s, 1H), 8.11 (d, J=2.1 Hz, 1H), 8.16 (s, 1H), 8.52 (d, J=2.7 Hz, 1H), 8.95 (s, 1H), 9.17 (s, 1H). MS (ESI+): 506.1 [M+H]$^+$

Step 5: Synthesis of 1-(4-chloro-3-(trifluoromethyl)phenyl)-3-(4-(5-fluoro-2-(1-methyl-pyrazol-4-yl)-pyridin-4-yl-oxy)phenyl)urea p-toluene sulfonate

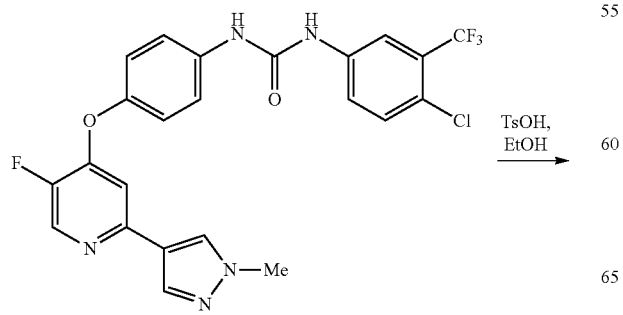

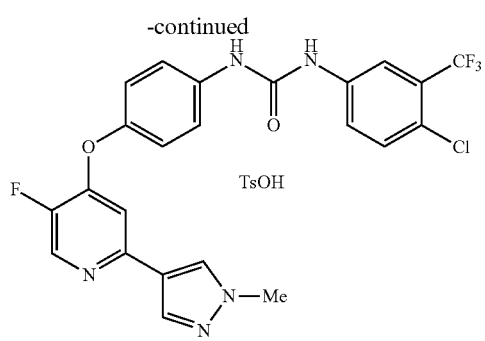

1-(4-Chloro-3-(trifluoromethyl)phenyl)-3-(4-(5-fluoro-2-(1-methyl-pyrazol-4-yl)-pyridin-4-yl-oxy)phenyl)urea (55 mg, 0.109 mmol) and p-toluenesulfonic acid monohydrate (25 mg, 0.131 mmol) were added to anhydrous ethanol (2 mL). The resultant mixture was heated to reflux, and anhydrous ethanol was added until the solid was completely dissolved. The resultant clear solution was filtrated, the filtrate was standing overnight, and then filtrated under suction, the resultant white solid was collected, and dried to get product as white solid (42 mg, yield: 57%).

1H NMR (300 MHz, DMSO) δ 9.28 (s, 1H), 9.08 (s, 1H), 8.64 (d, J=3.2 Hz, 1H), 8.23 (s, 1H), 8.12 (d, J=1.7 Hz, 1H), 7.90 (s, 1H), 7.74-7.55 (m, 4H), 7.50 (dd, J=5.3, 2.8 Hz, 2H), 7.26-7.07 (m, 5H), 3.84 (s, 3H), 2.29 (s, 1H).

Comparative Example 4

Compound No. FD-2013019

1-(4-chloro-3-(trifluoromethyl)phenyl)-3-(4-(2-(1-methyl-pyrazol-4-yl)-5-chloro-pyridin-4-yl-oxy)phenyl)urea

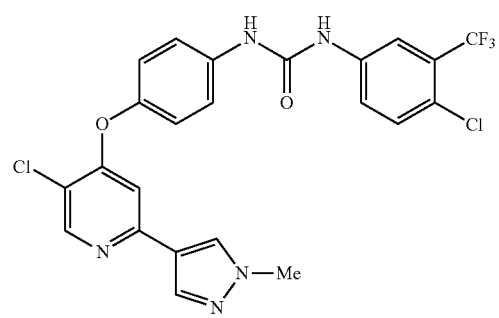 [SMILES: Cn1cc(-c2cc(Oc3ccc(NC(=O)Nc4ccc(Cl)c(C(F)(F)F)c4)cc3)c(Cl)cn2)cn1]

Preparation Method

Step 1: Synthesis of 2,5-dichloro-4-iodopyridine

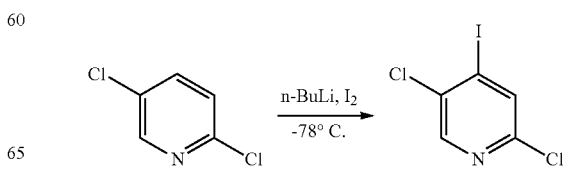

In a 100 mL three necked flask, 2,5-dichloropyridine (3.0 g, 20.3 mmol) was dissolved in anhydrous tetrahydrofuran (30 mL), and under the protection of nitrogen gas, the temperature was decreased to −78° C. After 30 minutes, a solution of 2.4M n-butyl lithium in n-hexane (8.9 mL, 21.3 mmol) was slowly added dropwise. After the addition, the reaction was carried out at the temperature for 90 minutes, and then a solution of iodine (6.13 g, 24.2 mmol) in anhydrous tetrahydrofuran (10 mL) was slowly added dropwise to the reaction system, then the temperature was increased to room temperature. Saturated ammonium chloride solution (100 mL) was added, and water (50 mL) was also added, then phase separation was performed, water phase was extracted separately with 50 mL, 40 mL, 200 mL ethyl acetate once. The organic phases were combined, and washed separately with saturated sodium thiosulfate solution (50 mL×2) and with saline solution (50 mL×2), dried with anhydrous sodium sulfate, filtrated, and concentrated to get crude product as yellow solid (4 g, yield: 72%). The crude product was directly used in the next step without further purification.

MS (ESI+): 273.9 [M+H]+

Step 2: Synthesis of 2,5-dichloro-4-(4-aminophenoxy)pyridine

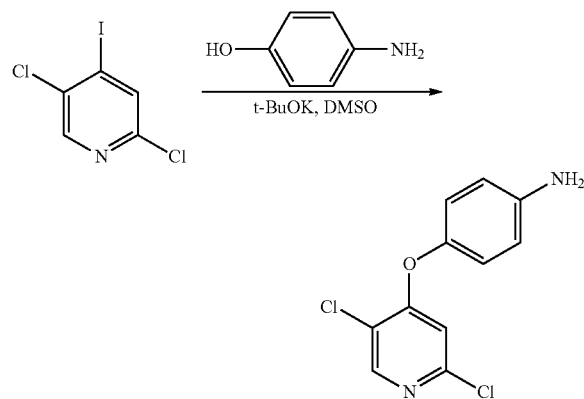

4-Aminophenol (1.59 g, 14.6 mmol) was dissolved in anhydrous dimethyl sulfoxide (30 mL), and purged with nitrogen gas for 10 minutes, potassium tert-butoxide (1.68 g, 15 mmol) was added, and then stirred at room temperature for 30 minutes, 2,5-dichloro-4-iodopyridine (4 g, 14.6 mmol) was added, then reacted at room temperature for 5 hours, TLC showed that the reaction was finished. Ethyl acetate (80 mL) was added, sufficiently stirred, then water (100 mL) was added. After phase separation, water phase was extracted with ethyl acetate (100 mL×3). The ethyl acetate phases were combined, washed with water (150 mL×2), washed with saline solution (100 mL×2), dried with anhydrous sodium sulfate, filtrated, and concentrated. The residue was purified by column chromatography (silica gel, petroleum ether:ethyl acetate=4:1, v/v) to get product as light yellow solid (0.34 g, yield: 9.1%).

MS (ESI+): 255.0 [M+H]+

Step 3: Synthesis of 4-(5-chloro-2-(1-methyl-pyrazol-4-yl)-pyridin-4-yl-oxy)aniline

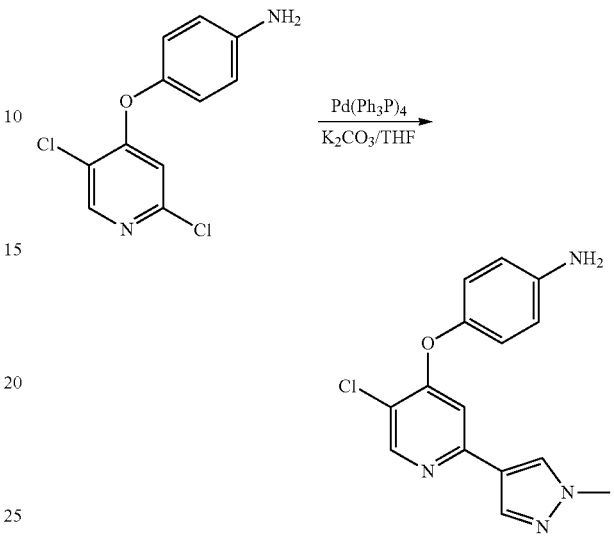

Under a protection of nitrogen gas, 2,5-dichloro-4-(4-aminophenoxy)pyridine (340 mg, 1.33 mmol) and 1-methylpyrazol-4-yl-boronic acid pinacol ester (278 mg, 1.33 mmol) were dissolved in tetrahydrofuran (THF, 8 mL), and potassium carbonate (548 mg, 3.97 mmol) and water (1.33 mL) were added, then tetrakis (triphenylphosphine) palladium catalyst (76 mg, 0.06 mmol) as a catalyst was added in dark, and then stirred at 85° C. for 24 hours, when TLC showed that the reaction was finished, cooled to room temperature, ethyl acetate and water were added (20 mL for each). After phase separation, water phase was extracted with ethyl acetate (20 mL×2). The ethyl acetate phases were combined, washed with saline solution (20 mL×2), dried with anhydrous sodium sulfate, filtrated, and concentrated. The residue was purified by column chromatography (silica gel, petroleum ether:ethyl acetate=4:1, v/v) to get product as light yellow solid (75 mg, yield: 19%).

MS (ESI+): 301.0 [M+H]+

Step 4: Synthesis of 1-(4-chloro-3-(trifluoromethyl) phenyl)-3-(4-(5-chloro-2-(1-methyl-pyrazol-4-yl)-pyridin-4-yl-oxy)phenyl)urea

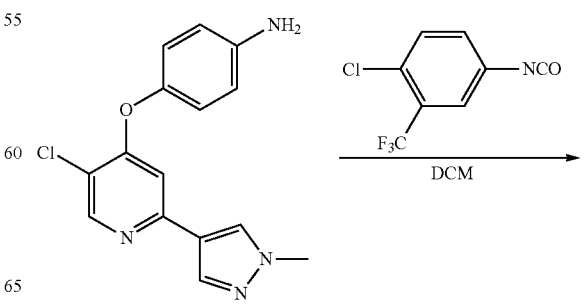

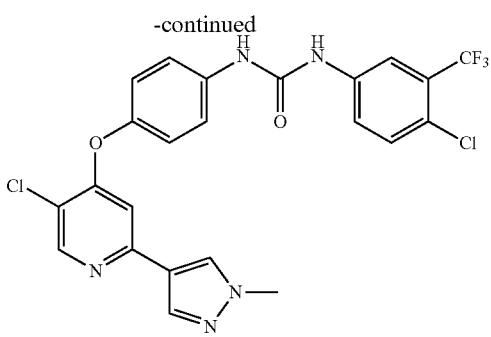

4-(5-Chloro-2-(1-methyl-pyrazol-4-yl)-pyridin-4-yl-oxy) aniline (75 mg, 0.25 mmol) was dissolved in dichloromethane (2 mL), and under a protection of nitrogen gas, 4-chloro-3-trifluoromethylphenyl isocyanate (67 mg, 0.3 mmol) was added, and then stirred at room temperature for 12 hours then a lot of solids were precipitated, then filtrated under suction, washed with dichloromethane, and dried to get product as white solid (78 mg, yield: 59.7%).

$^1$H NMR (300 MHz, DMSO-d$_6$): δ 3.82 (s, 3H), 6.98 (s, 1H), 7.18 (d, J=9.0 Hz, 2H), 7.59 (d, J=9.0 Hz, 2H), 7.63-7.66 (m, 2H), 7.82 (s, 1H), 8.12 (d, J=2.1 Hz, 1H), 8.22 (s, 1H), 8.59 (s, 1H), 9.05 (s, 1H), 9.25 (s, 1H). MS (ESI+): 522.1 [M+H]$^+$

Step 5: Synthesis of 1-(4-chloro-3-(trifluoromethyl) phenyl)-3-(4-(5-chloro-2-(1-methyl-pyrazol-4-yl)-pyridin-4-yl-oxy)phenyl)urea p-toluene sulfonate

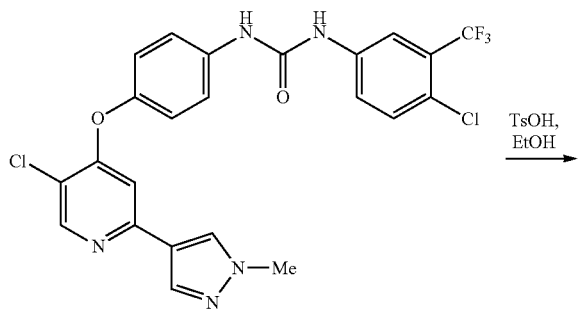

1-(4-Chloro-3-(trifluoromethyl)phenyl)-3-(4-(5-chloro-2-(1-methyl-pyrazol-4-yl)-pyridin-4-yloxy)phenyl)urea (70 mg, 0.134 mmol) and p-toluenesulfonic acid monohydrate (31 mg, 0.161 mmol) were added into anhydrous ethanol (2 mL). The resultant mixture was heated to reflux, and anhydrous ethanol was further added until the solid was completely dissolved. The resultant clear solution was filtrated, the filtrate was standing overnight, then filtrated under suction, the resultant white solid was collected, and dried to get product as white solid (57 mg, yield: 61%).

$^1$H NMR (300 MHz, DMSO) δ 9.25 (s, 1H), 9.05 (s, 1H), 8.59 (s, 1H), 8.22 (s, 1H), 8.12 (d, J=2.2 Hz, 1H), 7.87 (s, 1H), 7.72-7.54 (m, 4H), 7.48 (d, J=8.0 Hz, 2H), 7.18 (d, J=9.0 Hz, 2H), 7.11 (d, J=7.9 Hz, 2H), 6.98 (s, 1H), 3.82 (s, 3H), 2.29 (s, 3H).

Comparative Example 5

Compound No. FD-2013017

1-(4-chloro-3-(trifluoromethyl)phenyl)-3-(4-(2-(1-methyl-pyrazol-4-yl)-6-methoxy-pyridin-4-yl-oxy) phenyl)urea

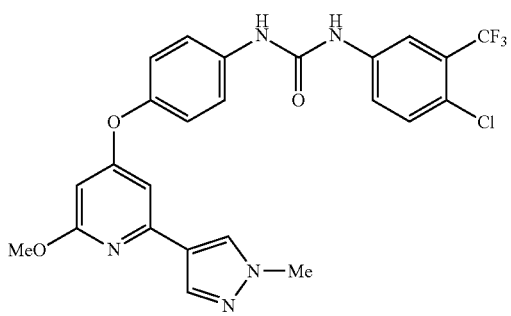 [SMILES: COc1cc(Oc2ccc(NC(=O)Nc3ccc(Cl)c(C(F)(F)F)c3)cc2)cc(-c2cnn(C)c2)n1]

Preparation Method

Step 1: 2,6-dichloro-4-(4-aminophenyl)pyridine

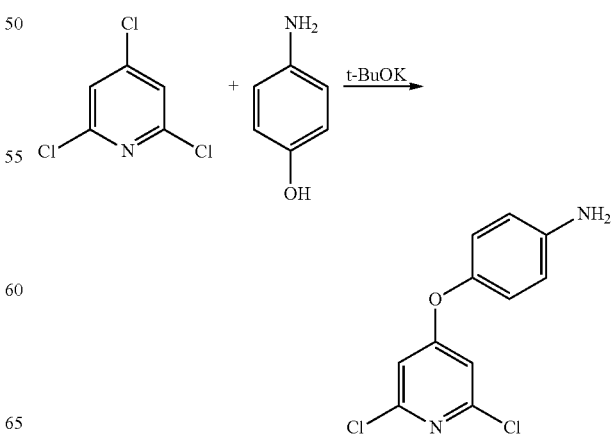

4-Aminophenol (2.39 g, 21.9 mmol) was dissolved in anhydrous dimethyl sulfoxide (30 mL), and purged with nitrogen gas for 10 minutes, and then potassium tert-butoxide (2.45 g, 21.9 mmol) was added, then stirred at room temperature for 30 minutes. 2,4,6-trichloropyridine (4 g, 21.9 mmol) was added and then reacted at 45° C. for 5 hours, TLC showed that the reaction was finished. Ethyl acetate (80 mL) was added, sufficiently stirred, then water (100 mL) was added, then phase separation was performed. Water phase was extracted with ethyl acetate (100 mL×3). The ethyl acetatephases were combined, washed with water (150 mL×2), washed with saline solution (100 mL×2), dried with anhydrous sodium sulfate, filtrated, and concentrated to get crude product as light yellow solid (5.1 g, yield: 91%). The crude product was directly used in the next step without further purification.

MS (ESI+): 255.0 [M+H]$^+$

Step 2: Synthesis of 2-chloro-6-methoxy-4-(4-aminophenoxy) pyridine

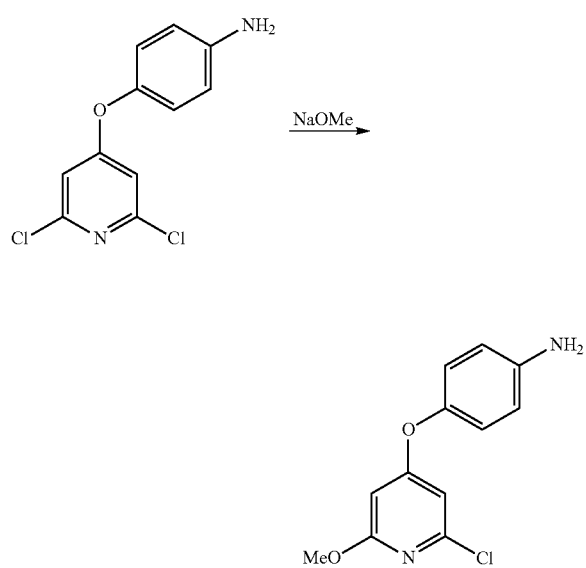

2,6-Dichloro-4-(4-aminophenyl)pyridine (7.2 g, 28.2 mmol) was dissolved in anhydrous methanol (50 mL), and sodium methoxide (1.52 g, 28.2 mmol) was added, then refluxing for 24 hours, and then distilled to dryness under reduced pressure. Water (100 mL) was then added. The resultant solution was extracted with ethyl acetate (100 mL×3), washed with saline solution (100 mL×2), dried with anhydrous sodium sulfate, filtrated, and concentrated. The residue was purified by column chromatography (petroleum ether:ethyl acetate 8:1) to get product as yellow solid (0.88 g, yield: 12%).

MS (ESI+): 251.0 [M+H]$^+$

Step 3: Synthesis of 4-(6-methoxy-2-(1-methyl-pyrazol-4-yl)-pyridin-4-yl-oxy) aniline

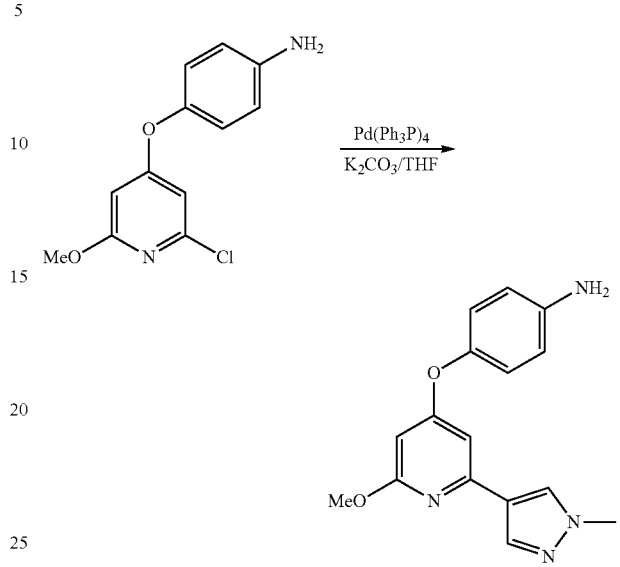

Under a protection of nitrogen gas, 2-chloro-6-methoxy-4-(4-aminophenoxy)pyridine (440 mg, 1.76 mmol) and 1-methylpyrazol-4-yl-boronic acid pinacol ester (368 mg, 1.76 mmol) were dissolved in tetrahydrofuran (THF, 8 mL), and potassium carbonate (726 mg, 5.25 mmol) and water (1.76 mL) were added, tetrakis(triphenylphosphine)palladium as a catalyst (100 mg, 0.08 mmol) was then added in dark, and stirred at 85° C. for 24 hours, then cooled to room temperature when TLC showed that the reaction was finished. Ethyl acetate and water (20 mL for each) were then added, then phase separation was performed. Water phase was extracted with ethyl acetate (20 mL×2), and the ethyl acetate phases were combined, washed with saline solution (20 mL×2), dried with anhydrous sodium sulfate, filtrated, and concentrated. The residue was purified by column chromatography (silica gel, petroleum ether:ethyl acetate=4:1, v/v) to get product as light yellow solid (400 mg, yield: 77%).

MS (ESI+): 297.2 [M+H]$^+$

Step 4: Synthesis of 1-(4-chloro-3-(trifluoromethyl)phenyl)-3-(4-(6-methoxy-2-(1-methyl-pyrazol-4-yl)-pyridin-4-yl-oxy)phenyl)urea

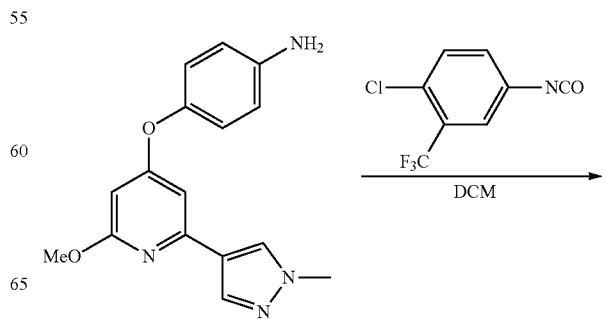

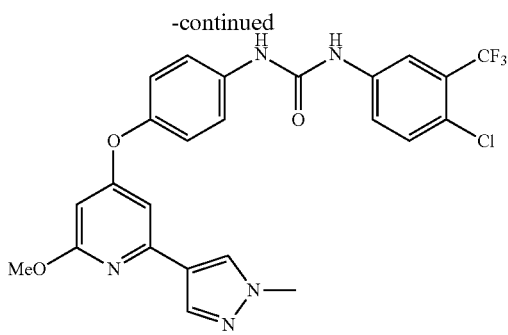

4-(6-Methoxy-2-(1-methyl-pyrazol-4-yl)-pyridin-4-yl-oxy)aniline (400 mg, 1.35 mmol) was dissolved in dichloromethane (2 mL), and under a protection of nitrogen gas, 4-chloro-3-trifluoromethylphenyl isocyanate (300 mg, 1.35 mmol) was added, stirred at room temperature for 12 hours, and then solids were precipitated, filtrated under suction, washed with dichloromethane, and dried to get product as white solid (300 mg, yield: 43%).

$^1$H NMR (300 MHz, DMSO-$d_6$): δ 3.84 (s, 3H), 3.85 (s, 3H), 6.25 (d, J=2.4 Hz, 1H), 7.00-7.03 (m, 1H), 7.12 (d, J=8.4 Hz, 2H), 7.51 (d, J=8.4 Hz, 2H), 7.60-7.68 (m, 2H), 7.86 (s, 1H), 8.07 (s, 1H), 8.13 (d, J=2.4 Hz, 1H), 8.94 (s, 1H), 9.23 (s, 1H). MS (ESI+): 518.1 [M+H]$^+$

Experimental Example 1: Determination of Compounds for the Inhibitory Activity of VEGFR2 Kinase 1. Materials and Devices EnVision 2104 multi-label microplate detector (PerkinElmer);
OptiPlate-384 White Opaque 384-well microwell plate (Cat. 6007290, PerkinElmer);
HTRF®KinEASE™-TK kit (Cat.62TKOPEC, Cisbio);
VEGFR2 (Cat: k2643, Sigma);
5× kinase buffer (Cat: PV3189, Invitrogen);
ATP 10 mM (Cat.PV3227, Invitrogen);
DTT 1 M (Cat.D5545, Sigma);
$MgCl_2$ 1 M (Cat.M8266, Sigma);
$MnCl_2$ 1 M (Cat.244589, Sigma);
Test Compound: Compound Prepared in Example
Control Compound: Compound Prepared in Comparative Example 2. Experimental Steps 2.1 Preparation of VEGFR2 Kinase Reagent

TABLE 1

Components and concentrations thereof in VEGFR2 kinase reaction system

| | | |
|---|---|---|
| Concentration of VEGFR2 kinase | Final concentration in the enzyme reaction step (10 μL) | 2 ng/well |
| ATP (μM) | | 5 μM |
| TK substrate-biotin | | 200 nM |
| Enzyme reaction time | | 20 minutes |
| Sa-XL665 | Final concentration in the complete reaction (20 μL) | 125 nM |
| TK Ab-cryptate | | 1:100 diluted |

1× kinase buffer: 1 mL 1× kinase buffer contained 200 μL 5× kinase buffer (Invitrogen), 5 μL, 1M $MgCl_2$, 1 μL 1M DTT, 1 μL 1M $MnCl_2$, and 793 μL dd$H_2$O;

5×TK substrate-biotin and ATP working fluid: as the concentrations of TK substrate-biotin and ATP, please refer to Table 1. TK substrate-biotin and ATP were diluted with 1× kinase buffer to 5 folds of the reaction concentrations;

5× kinase working fluid: as the concentration of VEGFR2 kinase, please refer to Table 1. 5× kinase working fluid was prepared with 1× Kinase buffer;

4× Sa-XL665 working fluid: as the concentration of Sa-XL665 (Cisbio) in the reaction, please refer to Table 1. The 4× Sa-XL665 working fluid was prepared with assay buffer (Cisbio);

4×TK Ab-cryptate working fluid: TK Ab-Cryptate (Cisbio) was 100-fold diluted with assay buffer (Cisbio), as working fluid;

2.2 Experimental Procedure

Experimental Procedure of HTRF KinEASE TK Kit

After all the reagents were prepared as described above, the reagents except for enzymes were equilibrated to room temperature, then adding samples were performed.

TK substrate-biotin, ATP, VEGFR2 kinase and a compound at a certain concentration were reacted in 1× kinase buffer at room temperature for 20 minutes. The concentration for a test compound was from 0 to 100 μM, and 2.5% DMSO was used as co-solvent. To all the reaction wells, 5 μl 4× Sa-XL665 working fluid and 5 μl 4×TK Ab-cryptate working fluid were added. After reacting at room temperature for 1 hours, fluorescence signal (excited at 320 nm, emitted at 665 nm, 615 nm) was detected by ENVISION detector (Perkinelmer). Based on the full-active well and the background signal well, the inhibition rate for each well was calculated, and the average value was used for duplicate wells. The half maximal inhibitory concentration ($IC_{50}$) for each test compound was fitted by professional software Graphpad PRISM 5.0.

Flow chart of adding samples is as follows:

| Enzymatic step | Kinase assay | Control | |
|---|---|---|---|
| (10 μL) | Sample | Negative | Positive |
| Compound | 4 μL | 4 μL 2.5% DMSO/kinase buffer | 4 μL 2.5% DMSO/kinase buffer |
| TK substrate-biotin | 2 μL | 2 μL | 2 μL |
| Kinase | 2 μL | 2 μL kinase buffer | 2 μL |
| The plate was sealed and incubated at room temperature for 10 minutes | | | |
| ATP | 2 μL | 2 μL | 2 μL |
| The plate was sealed and incubated at room temperature for 20 minutes | | | |
| Detection step (10 μL) | | | |
| Sa-XL665 | 5 μL | 5 μL | 5 μL |
| TK Ab-Cryptate | 5 μL | 5 μL | 5 μL |
| The plate was sealed and incubated at room temperature for 1 hours | | | |
| Excited at 320 nm, emitted at 665 nm, 615 nm | | | |

2.3 Data Analysis

Emission light ratio (ER)=665 nm emission signal/ 615 nm emission signal

Inhibition rate=$(ER_{positive}-ER_{sample})/(ER_{positive}-ER_{negative})*100\%$ 3. Experimental Results HTRF KinEASE TK kit was used to determine the $IC_{50}$ value of a compound for kinase VEGFR2. The final concentration of the compound started from 100 μM, and 4-fold gradient dilution was carried out to provide 10 concentrations. Duplicate wells were used for each concentration. The final concentration of DMSO was controlled to 1% in the reaction system. The experimental results were shown in Table 2 and FIG. 1.

TABLE 2

Determination of IC$_{50}$ of a compound according to the present invention for inhibitory activity of VEGFR2 kinase

| Compound | Initial No. | Structure | IC$_{50}$ (nM) |
|---|---|---|---|
| Example 1 | FD-2013015 | (structure with F on pyridine) | 28.60 |
| Example 2 | FD-2013018 | (structure with Cl on pyridine) | 55.52 |
| Example 3 | FD-2013024 | (structure with F on phenyl and Cl on pyridine) | 221.6 |
| Example 4 | FD-2013025 | (structure with CN on pyridine) | 68.55 |

TABLE 2-continued

Determination of IC$_{50}$ of a compound according to the present invention for inhibitory activity of VEGFR2 kinase

| Compound | Initial No. | Structure | IC$_{50}$ (nM) |
| --- | --- | --- | --- |
| Example 5 | FD-2013027 | (structure with Me substituent on pyridine) | 317.2 |
| Example 6 | FD-2013031 | (structure with NH$_2$ substituent on pyridine) | 214.7 |
| Example 7 | FD-2013033 | (structure with NHMe substituent on pyridine) | 655.9 |
| Example 8 | FD-2013037 | (structure with OMe substituent on pyridine) | 417.2 |

TABLE 2-continued

Determination of $IC_{50}$ of a compound according to the present invention for inhibitory activity of VEGFR2 kinase

| Compound | Initial No. | $IC_{50}$ (nM) |
|---|---|---|
| Comparative example 1 | Sorafenib (free base) | 89.63 |
| Comparative example 2 | FD-1210005 | 188.1 |
| Comparative example 3 | FD-2013016 | 436.7 |
| Comparative example 4 | FD-2013019 | 20475 |

TABLE 2-continued

Determination of IC$_{50}$ of a compound according to the present invention for inhibitory activity of VEGFR2 kinase

| Compound | Initial No. | | IC$_{50}$ (nM) |
|---|---|---|---|
| Comparative example 5 | FD-2013017 | 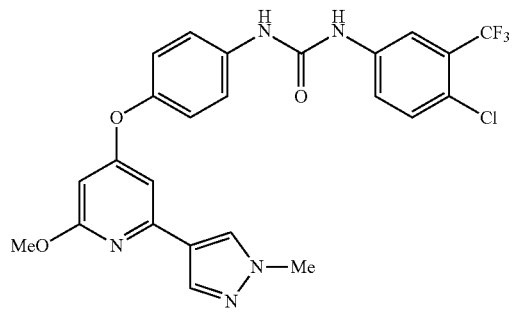 [SMILES: COc1cc(Oc2ccc(NC(=O)Nc3ccc(Cl)c(C(F)(F)F)c3)cc2)cc(-c2cnn(C)c2)n1] | 2392 |

4. Experimental Conclusion:

All the example compounds according to the present invention had an IC$_{50}$ value of below 1000, which indicated that the compounds according to the present invention had very excellent inhibitory activity of kinase VEGFR2, and could be studied as excellent antitumor drugs.

By comparison with the very excellent antitumor drug Sorafenib in the market, the preferred compounds of the present invention were 2-3 fold higher than the commercially available drug Sorafenib (Comparative compound 1) in terms of inhibitory activity of kinase VEGFR2, and were better than the compound (Comparative compound 2) disclosed in the Chinese patent application CN201110435847.9. The IC$_{50}$ value of the compound prepared in Example 1 of the present invention was 0.32- and 0.15-fold of that of Sorafenib (free base) and Comparative compound 2, respectively, i.e., its inhibitory activity was 3.13- and 6.6-fold of that of Sorafenib and Comparative compound 2, respectively. The IC$_{50}$ value of the compound prepared in Example 2 was 0.62- and 0.34-fold of that of Sorafenib (free base) and Comparative compound 2, respectively, i.e., its inhibitory activity was 1.61- and 3.4-fold of that of Sorafenib and Comparative compound 2, respectively. The IC$_{50}$ value of the compound prepared in Example 4 was 0.75- and 0.36-fold of that of Sorafenib (free base) and Comparative compound 2, respectively, i.e., its inhibitory activity was 1.3- and 2.7-fold of that of Sorafenib and Comparative compound 2, respectively. The IC$_{50}$ value of the compound prepared in Example 3 was 2.5-fold of that of Sorafenib (free base), i.e., its inhibitory activity was 1.5 fold of that of Sorafenib, and was comparable to that of Comparative compound 2, i.e., their inhibitory activity was comparable.

Therefore, it can be seen from the above experimental results that the compounds according to the present invention have very excellent inhibitory activity of VEGFR2 kinase.

By the comparison of the three substituents X3, X4, and X5 in Formula II of the present invention, the compounds according to the present invention are obviously better than Comparative example 3, 4, and 5.

Experimental Example 2: Determination of the Compounds According to the Present Invention for IC$_{50}$ of the In Vitro Anti-Proliferation of Tumor Cells 1. Materials and Methods Cell Strain:

MDA-MB-231 human mammary cancer cell strain (purchased from Shanghai Institute of Cell Biology, Chinese Academy of Sciences);

A498 human renal carcinoma cell strain (purchased from Shanghai Institute of Cell Biology, Chinese Academy of Sciences);

HCT116 human colon cancer cell strain (purchased from Shanghai Institute of Cell Biology, Chinese Academy of Sciences);

786-O human renal clear cell carcinoma cell strain (purchased from Shanghai Institute of Cell Biology, Chinese Academy of Sciences);

MiaPaCa-2 human pancreatic cancer cell strain (purchased from American ATCC);

SK-OV-3 human ovarian cancer cell strain (purchased from Shanghai Institute of Cell Biology, Chinese Academy of Sciences);

HepG2 human liver cancer cell strain (purchased from Shanghai Institute of Cell Biology, Chinese Academy of Sciences);

NCI-H460 Human large cell lung cancer cell strain (purchased from Shanghai Institute of Cell Biology, Chinese Academy of Sciences);

HL-60 human acute myeloid leukemia cell strain (purchased from Shanghai Institute of Cell Biology, Chinese Academy of Sciences);

Reagents and Consumptive Materials:

Cell Counting Kit-8 (Cat# CK04-13, Dojindo);

96-well plate (Cat#3599, Corning Costar);

fetal bovine serum (Cat#10099-141, GIBCO);

Culture media (Invitrogen) in Table 3;

Desk-top ELISA instrument Spectra Max M5 Microplate Reader (Molecular Devices);

Test Compounds: Compounds Prepared in Examples;
Control Compounds: Compounds Prepared in Comparative Examples;

2. Experimental Steps 2.1 Reagent Preparation

TABLE 3

Preparation of Culture medium

| Cell strain | Culture medium |
|---|---|
| 786-O | RPMI 1640 + 10% FBS |
| MDA-MB-231 | RPMI 1640 + 10% FBS |
| A498 | EMEM + 10% FBS |
| HCT116 | DMEM + 10% FBS |
| SK-OV-3 | McCoy's 5A + 10% FBS |
| MiaPaCa-2 | RPMI 1640 + 10% FBS |
| HepG2 | EMEM + 10% FBS |
| NCI-H460 | RPMI 1640 + 10% FBS |
| HL-60 | RPMI 1640 + 10% FBS |

Preparation of a compound: the compound was diluted with DMSO to a final concentration of 10 mM.

2.2 Cell Culture a) Cells in logarithmic growth phase were collected, counted, and re-suspended in complete medium.

b) The concentration of cells was adjusted to a suitable concentration, and the cells were seeded to a 96-well plate at 100 μl cell suspension per well.

c) The cells were incubated in an incubator at 37° C., 100% relative humidity, 5% $CO_2$ for 24 hours.

2.3 $IC_{50}$ Assay a) Cells in logarithmic growth phase were collected, counted, and re-suspended in complete medium. The concentration of cells was adjusted to a suitable concentration (determined depending on the result of optimization experiment of cell density), and the cells were seeded to a 96-well plate at 100 μl cell suspension per well. The cells were incubated in an incubator at 37° C., 100% relative humidity, 5% $CO_2$ for 24 hours.

b) A test compound was diluted with the culture medium to 500 μM, and then gradient dilution was performed for 8 times. Cells were added at 25 μl/well. The final concentrations of the compound was in a range from 100 μM and 0 μM, 4-fold diluted, including 10 concentrations.

c) The cells were incubated in an incubator at 37° C., 100% relative humidity, 5% $CO_2$ for 72 hours.

d) The culture medium was withdraw and discarded, the complete medium containing 10% CCK-8 was added, and then the cells were incubated in an incubator at 37° C. for 2-4 hours.

e) After gentle shaking, absorbance was determined at a wavelength of 450 nm by SpectraMax M5 Microplate Reader, and absorbance at a wavelength of 650 nm was used as reference to calculate inhibition rate.

2.4 Data Processing

Tumor cell growth inhibition rate of a drug is calculated by the following formula:

Tumor cell growth inhibition rate (%)=$[(A_c-A_s)/(A_c-A_b)]\times 100\%$.

A: Absorbance of a sample (cell+CCK-8+Test compound);

$A_c$: Absorbance of negative control (Cell+CCK-8+DMSO);

$A_b$: Absorbance of positive control (Culture medium+CCK-8+DMSO);

$IC_{50}$ curve was fitted and $IC_{50}$ value was calculated by professional software GraphPad Prism 5.0.

3. Experimental Result

In the experiment, the compounds according to the present invention were determined for their $IC_{50}$ values of in vitro anti-proliferation of tumor cell strains. The final concentrations of the compounds was in a range from 100 μM and 0 μM, 4-fold diluted, including 10 concentrations. The experimental results were shown in Table 4.

TABLE 4

| | $IC_{50}$ (μM) | | |
|---|---|---|---|
| Cell line | Example 1 (FD-2013015) | Example 2 (FD-2013018) | Comparative example 1 (Sorafenib) |
| SK-OV-3 | 7.141 | 5.762 | 17.906 |
| HCT-116 | 2.774 | 3.159 | 4.561 |
| 786-O | 2.432 | 2.768 | 4.509 |
| A498 | 4.945 | 4.710 | 5.492 |
| MDA-MB-231 | 2.822 | 3.047 | 10.002 |
| MiaPaCa-2 | 2.036 | 2.339 | 3.061 |
| HepG2 | 0.721 | 0.808 | 0.947 |
| NCI-H460 | 0.939 | 1.050 | 1.272 |
| HL-60 | 17.139 | 18.227 | 22.012 |

4. Experimental Conclusion:

In the experiment on anti-proliferation of tumor cells in vitro, the compounds according to the present invention had the 50% inhibitory concentration $IC_{50}$ between 0 and 20, which indicated the compounds according to the invention had very excellent inhibitory activity of tumor cells in vitro, and could be studied as excellent anti-tumor drugs.

By comparison with the very excellent anti-tumor drug Sorafenib in the market, the compounds according to the invention were significantly superior to the commercially available drug Sorafenib in terms of half maximal inhibitory concentration ($IC_{50}$) of the different tumor cell lines such as SK-OV-3, HCT-116, 786-O, and MDA-MB-231 (e.g., in MDA-MB-231 cell line, the $IC_{50}$ of the compound prepared in Example 1 was 0.28-fold of that of Sorafenib, and the $IC_{50}$ of the compound prepared in Example 2 was 0.30-fold of Sorafenib); the half maximal inhibitory concentration ($IC_{50}$) of the tumor cell lines such as A498, MiaPaCa-2, HepG2, NCI-H460, and HL-60 was comparable to that of the commercially available drug Sorafenib.

The experiment demonstrates that the compounds according to the present invention have excellent anti-proliferation activity for tumor cells.

Experimental Example 3: Study on Pharmacokinetics of the Compounds According to the Present Invention in Mice 1. Materials and Methods 1.1 Test Compound Compounds prepared in Examples, Comparative examples of the present invention 1.2 Experimental Animal CD-1 mouse, female, weighed 28-35 g.

1.3 Administration Route

Administration route: intravenous injection (IV); per os (PO).

Fasting condition: free access to water, no fasting.

2. Experimental Method 2.1 Administration and Sample Collection 2.1.1 Administration The mice were weighed before administration, and the administration volume was calculated based on their body weights (IV group: 4 mL/kg; PO group: 10 mL/kg).

Administration route and dose: Intravenous (IV) group: 1 mg/kg; Oral (PO) group: 5 mg/kg.

Sample: Plasma.

Animal grouping: 3 mice/group, an IV group and a PO group for each test compound.

2.1.2 Sample Collection

After administration, 30 μL whole blood was collected from rim of the eyes of mice in the IV group at each pre-determined time point (5 min, 15 min, 30 min, 1 h, 2 h, 4 h, 8 h, 24 h), and 30 μL whole blood was collected from rim of the eyes of mice in the PO group at each pre-determined time point (15 min, 30 min, 1 h, 2 h, 4 h, 8 h, 24 h). The whole blood was centrifuged (6,000 rpm, 5 min) to get blood plasma. All the blood plasma samples were stored in a refrigerator of −80° C. for further analysis.

2.2 Quantitative Analysis Method

Conditions of LC/MS/MS was as follows:

Ionization mode: ESI, positive ion;

Detection Mode: MRM;

Quantitative ion FD2012015: 506.12/270.20; Internal standard (terfenadine): 472.40/436.40;

Sample treatment: Protein was precipitated by using a solution of 50 ng terfenadine in acetonitrile solution;

Sample: CD-1 mouse plasma (anticoagulated by using EDTA); Sample volume: 20 μL;

Chromatographic column: ACE C4 column (50 mm*2.1 mm, 5 micron)

Mobile phase: gradient elution, mobile phase A was water (containing 0.1% formic acid), mobile phase B was acetonitrile (containing 0.1% formic acid);

Flow rate (mL/min): 0.9;

Column temperature (° C.): room temperature;

Injection volume (μL): 5;

Time (min): 2.0.

3. Data Processing

Pharmacokinetic parameters were estimated according to non-compartment model (calculated by WinNonlin software):

IV paramater: $t_{1/2}$ (hr); $C_0$ (ng/mL); $AUC_{last}$ (hr*ng/mL); $AUC_{Inf}$ (hr*ng/mL); AUC Extr (%); Vz (L/kg); Vss (L/kg); CL (mL/min/kg); MRT (hr).

PO parameter: $t_{1/2}$ (hr); $t_{max}$ (hr); $C_{max}$ (ng/mL); $AUC_{last}$ (hr*ng/mL); $AUC_{Inf}$ (hr*ng/mL); AUC Extr (%); MRT (hr); AUC/D (hr*mg/mL); F (%).

4. Experimental Results:

TABLE 5

Pharmacokinetic parameters of the compounds according to the present invention after oral administration (average value from three mice for each group)

| | $C_{max}$ (ng/mL) | $AUC_{last}$ (hr*ng/mL) | F (%) |
|---|---|---|---|
| Example 1 | 1913 | 39610 | 90.3 |
| Example 2 | 3007 | 56618 | 82.9 |
| Sorafenib | 1150 | 18920 | 78.6 |

Note:
$C_{max}$: peak concentration;
$AUC_{last}$: Area under the curve;
F: Oral bioavailability 5. Experimental Conclusion:

The compounds of Example 1 and 2 were significantly superior to the commercially available drug Sorafenib in terms of data such as metabolic stability, peak concentration, area under the curve of concentration-time, and oral bioavailability, and therefore were very perspective in clinic application. It indicated that after introduction of a substituent at position X3 of Formula I, the substituent (which is hydrogen at position X3 of Comparative compounds 2, 3, 4) blocked the site to be easily metabolized, enhanced the metabolic stability of the compounds, and ensured high blood concentration of the compounds in vivo, so as to further enhanced the efficacy of the compounds according to the present invention.

Experimental Example 4

1. Cell Culture

786-O cells were cultured in RPMI-1640 culture medium containing inactivated 10% fetal bovine serum, 100 Um' penicillin and 100 μg/ml streptomycin as well as 2 mM glutamine in an incubator at 37° C., 5% $CO_2$. During cell culture, the initial concentration was $5 \times 10^5$ cells/ml, and the cells were separated into other bottles every 3 to 4 days when the cells reached a cell density of 100%. The tumor cells in logarithmic growth phase were used in tumor inoculation in vivo.

2. Inoculation and Grouping of Tumor Cells

Female SCID-Beige nude mice (SPF grade) was inoculated subcutaneously at right lateral thorax with 786-O tumor cells re-suspended in PBS at $8 \times 10^6$ cells/0.1 ml. When the tumor grew into a volume of 800 $mm^3$, under aseptic conditions, tumor was peeled off. The well grown tumor tissues were cut into tumor mass with a size of $2 \times 2 \times 2$ $mm^3$, and then were used to inoculate animal subcutaneously. When the tumor grew to a volume of about 100 $mm^3$, the mice were grouped and administered, 5 groups in total, 8 mice per group.

3. Measurement of Tumor and Experimental Indexes

The volume of tumor was measure by using Vernier caliper twice a week. The long diameter and short diameter of tumor were measured. The volume was calculated by the formula: volume=0.5×long diameter×short $diameter^2$. After the final measurement, the animal was sacrificed and the tumor was peeled off and weighed. Based on the tumor weight of each group, tumor growth-inhibiting rate (TGI) was calculated. Tumor growth-inhibiting rate (TGI)=(1−T/C)×100%, wherein T represented average tumor weight of drug administration group; C represented average tumor weight of negative control group. The data was effectiveness when TGI≥60% and $p<0.05$ by statistical analysis.

TABLE 6

Tumor-inhibiting effect of FD-2013018 on 786-O humanized renal clear cell xenograft tumor-bearing mice (tumor weight)

| Group | Administration dose | Administration route | Animal number Beginning/end | Tumor weight (mg)[a] Mean ± S.E | TGI (%) | P[b] |
|---|---|---|---|---|---|---|
| Solvent control | Blank solvent[c] | po, QD × 14 days | 8/8 | 206 ± 47 | — | — |
| FD-2013018 | 10 mg/kg | po, QD × 14 days | 8/8 | 37 ± 20 | 82 | <0.001 |
| FD-2013018 | 20 mg/kg | po, QD × 14 days | 8/8 | 32 ± 15 | 85 | <0.001 |
| FD-2013018 | 40 mg/kg | po, QD × 14 days | 8/8 | 16 ± 12 | 92 | <0.001 |

Note:
[a]Mean ± Standard error;
[b]compared to solvent control;
[c]Blank solvent: solvent DMA:Solutol HS-15:$H_2O$ = 5:5:90 (a ratio by volume) (DMA was dimethyl acetamide, Solutol HS-15 was purchased from BASF, CAS: 61909-81-7); FD-2013018 was in a free form; po meant per os, QD meant once a day;
P: group 2 (10 mg/kg) vs. group 3 (20 mg/kg) = 0.999; group 2 vs. group 4 (40 mg/kg) = 0.386; Group 3 vs. group 4 = 0.270.

Experimental Example 5

1. Cell Culture

HCT116 cells were cultured in McCoy's 5a culture medium containing inactivated 10% fetal bovine serum, 100 Um' penicillin and 100 μg/ml streptomycin as well as 2 mM glutamine in an incubator at 37° C., 5% $CO_2$. During cell culture, the initial concentration was 5×10⁵ cells/ml, and the cells were separated into other bottles every 3 to 4 days when the cells reached a cell density of 100%. The tumor cells in logarithmic growth phase were used in tumor inoculation in vivo.

2. Inoculation and Grouping of Tumor Cells

Balb/c nude mice was inoculated subcutaneously at right lateral thorax with HCT116 tumor cells re-suspended in PBS at 1.0×10⁷ cells/0.1 ml. When the tumor grew into a volume of 800 mm³, the animal was sacrificed and under aseptic conditions, tumor was peeled off. The well grown tumor tissues were cut into tumor mass with a size of 2×2×2 mm³, and then were used to inoculate animal at right lateral thorax subcutaneously. 60 animals were inoculated. When the tumor grew into a volume of about 110 mm³, the mice were grouped and administered, 5 groups in total, 8 mice per group.

3. Measurement of Tumor and Experimental Indexes

The volume of tumor was measured by using Vernier caliper twice a week. The long diameter and short diameter of tumor were measured. The volume was calculated by the formula: volume=0.5× long diameter×short diameter². After the final measurement, the animal was sacrificed and the tumor was peeled off and weighed. Based on the tumor weight, tumor growth-inhibiting rate (TGI) was calculated. Tumor growth-inhibiting rate (TGI)=(1−T/C)×100%, wherein T represented average tumor weight of test compound group; C represented average tumor weight of solvent control group. When the assay was finished, the experimental animal was subjected to euthanasia.

TABLE 7

Tumor-inhibiting effect of FD-2013018 on HCT116 xenograft tumor-bearing mice (tumor weight)

| Group | Administration dose | Administration route | Number of Animals Beginning/end | Tumor weight (D27, g)[a] Mean ± S.E | TGI (%) | P[b] |
|---|---|---|---|---|---|---|
| Solvent control | Blank control | po, QD × 14 day | 8/8 | 0.961 ± 0.130 | — | — |
| FD-2013018 | 10 mg/kg | po, QD × 14 day | 8/8 | 0.153 ± 0.078 | 84.1 | <0.001 |
| FD-2013018 | 20 mg/kg | po, QD × 14 day | 8/8 | 0.104 ± 0.035 | 89.1 | <0.001 |
| FD-2013018 | 40 mg/kg | po, QD × 14 day | 8/8 | 0.077 ± 0.043 | 92.0 | <0.001 |

Note:
[a]Mean ± Standard error;
[b]compared to control group; FD-2013018 was in a free form; blank solvents was the same as the one defined in Table 6;
P: Group 2 (10 mg/kg) vs. Group 3 (20 mg/kg) = 0.687; Group 2 vs. Group 4 (40 mg/kg) = 0.248; Group 3 vs. Group 4 = 0.807.

Comparative Experimental Example 1

Sunitinib, prepared by the method disclosed in patent WO0160814 A1.

Animal Model Preparation:

The well grown 786-O solid tumor was cut into a mass of an average volume of about 1 mm³ under aseptic conditions, and was used to inoculate nude mouse at axillary cavity of right forelimb subcutaneously via a trocar. The tumor growth state was observed regularly until the tumor grew into a volume of 250~550 mm³.

Grouping and Administration:

Animals with tumors of a too large or too small volume and an irregular shape were discarded. Tumor-bearing mice with a tumor volume of 250~550 mm³ in a good state were selected, 48 mice in total, and were divided into 6 groups, which were 1 solvent control group, 3 positive control groups, and 2 test sample groups. Both the positive control group and the test sample group were administered intragastrically once a day; the solvent control group was administered with 12.5% ethanol & 12.5% water solution of polyoxyethylene castor oil once a day; intragastrical volume was 10 mL/kg.

In the period of administration, tumor diameter was measured twice every week, tumor volume was calculated, and animal body weight was recorded. Animal state was observed when administered, and abnormal state was recorded.

Animal Sacrifice:

Animal was sacrificed with $CO_2$, and tumor was peeled off, weighed, and photographed. Animal was subjected to gross anatomy, and organs were observed by eyes to find if they were normal or not.

Observation Indexes:

Tumor weight inhibiting rate (IR)=$(W_C-W_T)/W_C$

Wherein $W_C$ and $W_T$ represented the average tumor weight of solvent control group and the average tumor weight of drug administration group, respectively.

$BW_0$ represented the body weight of animal weighed when grouping (i.e., d0), $BW_t$ represented the body weight of animal weighed every time. If body weight-decreasing rate was a negative value, it meant that body weight increases.

Statistic Method:

Experimental data was subjected to calculation and relevant statistic processing by Microsoft Office Excel 2003 software. Unless otherwise specified, data was represented as Mean±Standard Error (Mean±S.E), and t-test is used in the comparison between two groups.

Comparative Experiment Example 2

Animal Model Preparation

Under aseptic conditions, the well grown human HCT-116 cell suspension in logarithmic growth phase was used to inoculate nude mouse at axillary cavity of right forelimb subcutaneously via an injector. The tumor growth state was observed regularly until the tumor grew to a volume of 100~300 mm³.

Grouping and Administration:

48 Tumor-bearing mice with a tumor volume of 100~300 mm³ were selected and divided into 6 groups, which were 1 solvent control group, 3 positive control groups, and 2 test sample groups. Both the positive control group and the test sample group were administered intragastrically once a day; the solvent control group was administered with 12.5% ethanol & 12.5% water solution of polyoxyethylene castor oil once a day; intragastrical volume was 10 mL/kg.

In the period of administration, tumor diameter was measured twice every week, tumor volume was calculated, and animal body weight was recorded. Animal state was observed when administered, and abnormal state was recorded.

Animal Sacrifice:

Animal was sacrificed with $CO_2$, and tumor mass was peeled off, weighed, and photographed. After photographed, each tumor mass was cut into two parts, wherein one was stored in 4% paraformaldehyde, and the other was packaged into a freezing tube, and frozen in liquid nitrogen. Animal was subjected to gross anatomy, and organs were observed by eyes to find if they were normal or not.

Observation Indexes:

Tumor weight inhibiting rate (IR)=$(W_C-W_T)/W_C$ wherein $W_C$ and $W_T$ represented the average tumor weight of solvent control group and the average tumor weight of drug administration group, respectively.

Statistic Method:

Experimental data was subjected to calculation and relevant statistic processing by Microsoft Office Excel 2003 software. Unless otherwise specified, data was represented as Mean±Standard Error (Mean±S.E.), and t-test is used in the comparison between two groups.

TABLE 8

Effect of FD-1210005 on tumor weight of human renal cancer 786-O transplantation nude mice

| Group No. | Dose (mg/kg) | Administration route | Number of Animals Beginning/end | Tumor weight (g) Mean ± S.E | Tumor-inhibiting rate % |
|---|---|---|---|---|---|
| Solvent control | solvent | po, QD × 14 days | 8/8 | 0.9356 ± 0.1126 | — |
| Sunitinib, 40, QD | 40 | po, QD × 14 days | 8/8 | 0.1825 ± 0.0213** | 80.49% |
| Sorafenib, 20, QD | 20 | po, QD × 14 days | 8/8 | 0.5239 ± 0.1038* | 44.01% |
| Sorafenib, 60, QD | 60 | po, QD × 14 days | 8/8 | 0.4407 ± 0.0581** | 52.89% |
| FD-1210005, 20, QD | 20 | po, QD × 14 days | 8/8 | 0.1892 ± 0.0253** | 79.78% |
| FD-1210005, 60, QD | 60 | po, QD × 14 days | 8/6 | 0.1897 ± 0.0192** | 79.73% |

Note:
1. Compared to solvent control group,
*P < 0.05,
**P < 0.01;
2. In the experiment, sorafenib was in a form of p-toluenesulfonate thereof, FD-1210005 was in a free form.

TABLE 9

Effect of FD-1210005 on tumor weight of human colon cancer HCT-116 transplantation nude mice

| Group | Dose (mg/kg) | Administration regimen | Number of animals beginning/end | Tumor weight (g) Mean ± S.E | Tumor-inhibiting rate % |
|---|---|---|---|---|---|
| Solvent control | Solvent | Ig, QD × 17 day | 8/8 | 0.9924 ± 0.1112 | — |
| Sunitinib, 40, QD | 40 | Ig, QD × 17 day | 8/8 | 0.3890 ± 0.0453** | 60.80% |
| Sorafenib, 20, QD | 20 | Ig, QD × 17 day | 8/8 | 0.5628 ± 0.0617** | 43.28% |
| Sorafenib, 60, QD | 60 | Ig, QD × 17 day | 8/8 | 0.4409 ± 0.0857** | 55.57% |
| FD-1210005, 20, QD | 20 | Ig, QD × 17 day | 8/8 | 0.3283 ± 0.0404** | 66.91% |
| FD-1210005, 60, QD | 60 | Ig, QD × 17 day | 8/8 | 0.2829 ± 0.0309** | 71.49% |

Note:
1. Compared to Solvent control,
*P < 0.05,
**P < 0.01;
2. "—" represented no data.
3. In the experiment, sorafenib was in a form of p-toluenesulfonate thereof, and FD-1210005 was in a free form.

The study results of in vivo antitumor experiment showed that the compound prepared in Example 2 (FD-2013018) reached an tumor-inhibiting effect of 82% and 84.1% for 786-O and HCT116 xenograft tumor-bearing mice at a dose of 10 mg/kg, respectively, and even reached an tumor-inhibiting effect of 92% at a dose of 40 mg/kg; while Comparative compound 2 (FD-2010005) reached an tumor-inhibiting effect of 80% and 67% for 786-O and HCT116 xenograft tumor-bearing mice at a dose of 20 mg/kg, respectively, and only reached an tumor-inhibiting effect of 80% and 71% at a dose of 60 mg/kg, respectively. The data showed that the compound prepared in Example 2 (FD-2013018) was superior to Comparative compound 2 (FD-1210005) in terms of in vivo antitumor activity, and had a lower effective dose and a stronger antitumor activity.

To sum up, the compounds according to the present invention have very strong antitumor activity in vitro and in vivo, and particularly excellent pharmacokinetic characteristics. By comparison with Sorafenib and the compound of Comparative example 2, the compounds according to the present invention have stronger antitumor activity in vitro and in vivo, and better pharmacokinetic characteristics.

Although the embodiments of the present invention are described in detail, a person skilled in the art would understand that according to the teachings of the disclosures of the present invention, those details can be modified and replaced, and these modifications and alterations all will fall in the protection scope of the present invention. The scope of the present invention is defined by the claims and any equivalent thereof.

The invention claimed is:

1. A polysubstituted pyridine compound of Formula I, or a hydrate, a solvate or a pharmaceutically acceptable salt thereof, Formula I

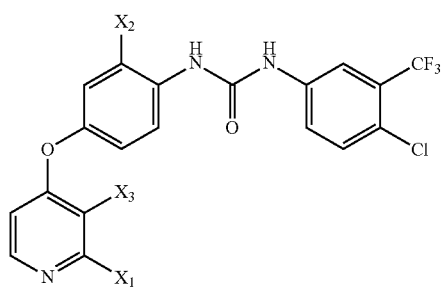

wherein:
$X_1$ is

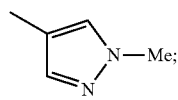

$X_2$ is selected from the group consisting of F and H;
$X_3$ is selected from the group consisting of F, Cl and —CN.

2. The polysubstituted pyridine compound, or a hydrate, a solvate or a pharmaceutically acceptable salt thereof according to claim 1, wherein the polysubstituted pyridine compound of Formula I is selected from the group consisting of the following compounds:

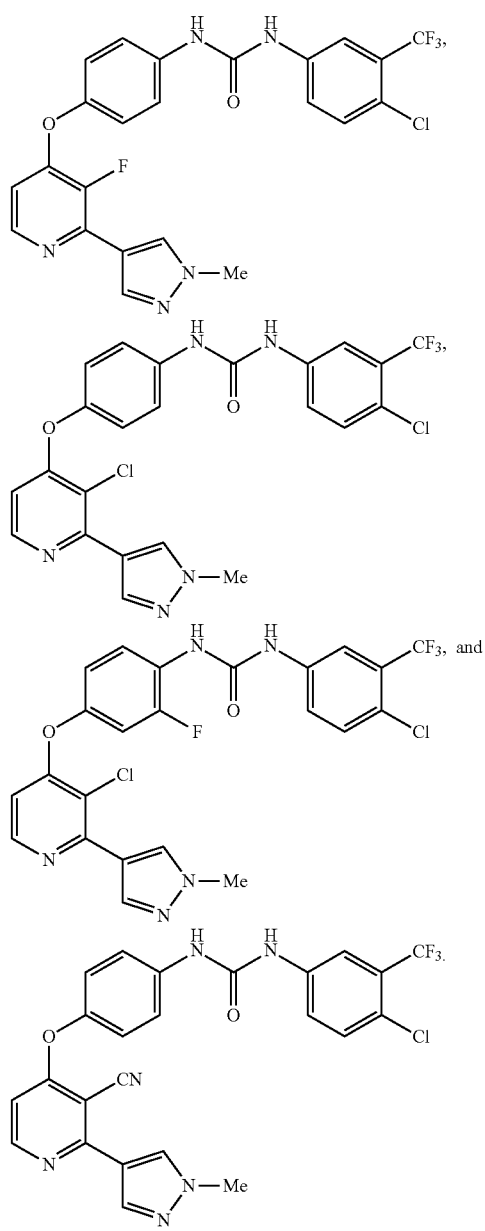

3. The polysubstituted pyridine compound, or a hydrate, a solvate or a pharmaceutically acceptable salt thereof according to claim 1, wherein the pharmaceutically acceptable salt of the polysubstituted pyridine compound of Formula I is selected from the group consisting of: hydrochloride, hydrobromide, sulphate, phosphate, methanesulfonate, trifluoromethanesulfonate, benzene sulfonate, p-toluenesulfonate, 1-naphthalenesulfonate, 2-naphthalenesulfonate, acetate, trifluoroacetate, malate, tartrate, citrate, lactate, oxalate, succinate, fumarate, maleate, benzoate, salicylate, phenyl acetate and mandelate.

4. A pharmaceutical composition, comprising the polysubstituted pyridine compound, or a hydrate, a solvate or a pharmaceutically acceptable salt thereof according to claim 1, and a pharmaceutically acceptable adjuvant.

* * * * *